(12) United States Patent
Fouda et al.

(10) Patent No.: US 10,533,411 B2
(45) Date of Patent: Jan. 14, 2020

(54) ELECTROMAGNETIC (EM) DEFECT DETECTION METHODS AND SYSTEMS EMPLOYING DECONVOLVED RAW MEASUREMENTS

(71) Applicant: HALLIBURTON ENERGY SERVICES, INC., Houston, TX (US)

(72) Inventors: Ahmed E. Fouda, Houston, TX (US); Reza Khalaj Amineh, Houston, TX (US); Luis Emilio San Martin, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 167 days.

(21) Appl. No.: 15/533,349

(22) PCT Filed: May 13, 2016

(86) PCT No.: PCT/US2016/032498
§ 371 (c)(1),
(2) Date: Jun. 5, 2017

(87) PCT Pub. No.: WO2017/196371
PCT Pub. Date: Nov. 16, 2017

(65) Prior Publication Data
US 2018/0106141 A1  Apr. 19, 2018

(51) Int. Cl.
*E21B 47/00* (2012.01)
*E21B 47/10* (2012.01)
(Continued)

(52) U.S. Cl.
CPC ............ *E21B 47/0006* (2013.01); *G01B 7/10* (2013.01); *G01N 17/04* (2013.01); *G01V 3/28* (2013.01); *G01V 3/38* (2013.01); *E21B 34/06* (2013.01)

(58) Field of Classification Search
CPC .... E21B 47/00; E21B 47/0006; E21B 47/082; E21B 47/10; G01V 3/18
See application file for complete search history.

(56) References Cited

U.S. PATENT DOCUMENTS

| | | |
|---|---|---|
| 4,292,588 A | 9/1981 | Smith |
| 4,292,589 A | 9/1981 | Bonner et al. |
| | (Continued) | |

FOREIGN PATENT DOCUMENTS

WO   2015/157268   10/2015

OTHER PUBLICATIONS

PCT International Search Report and Written Opinion, dated Jan. 6, 2017, Appl No. PCT/US2016/032498, "Electromagnetic (EM) Defect Detection Methods and Systems Employing Deconvolved Raw Measurements," Filed May 13, 2016.
(Continued)

*Primary Examiner* — Catherine Loikith
(74) *Attorney, Agent, or Firm* — Benjamin Fite; C. Tumey Law Group PLLC

(57) ABSTRACT

A method includes deploying an electromagnetic (EM) defect detection tool in a downhole environment having a plurality of tubular strings with different diameters. The method also includes receiving raw measurements collected by the EM defect detection tool. The method also includes deconvolving the raw measurements with another input to obtain deconvolved raw measurements. The method also includes using the deconvolved raw measurements to determine a defect in at least one of the plurality of tubular strings. The method also includes performing, by a device, an operation in response to the determined defect.

18 Claims, 18 Drawing Sheets

(51) Int. Cl.
    *G01V 3/18*     (2006.01)
    *G01V 3/38*     (2006.01)
    *G01B 7/06*     (2006.01)
    *G01N 17/04*     (2006.01)
    *G01V 3/28*     (2006.01)
    *E21B 34/06*     (2006.01)

(56) References Cited

U.S. PATENT DOCUMENTS

| | | |
|---|---|---|
| 5,233,297 A | 8/1993 | Lara |
| 5,987,385 A | 11/1999 | Varsamis et al. |
| 6,291,992 B1 | 9/2001 | Van Andel et al. |
| 7,960,969 B2 | 6/2011 | Mouget et al. |
| 8,958,989 B2 | 2/2015 | Legendre et al. |
| 9,060,689 B2 | 6/2015 | Tearney |
| 2004/0207389 A1 | 10/2004 | Nieminen et al. |
| 2005/0182613 A1 | 8/2005 | Kwun et al. |
| 2007/0108981 A1* | 5/2007 | Banning-Geertsma ............ G01V 3/28 324/338 |
| 2008/0210010 A1 | 9/2008 | Orth et al. |
| 2009/0195244 A1 | 8/2009 | Mouget et al. |
| 2010/0017137 A1 | 1/2010 | Legendre et al. |
| 2010/0121578 A1 | 5/2010 | Davis |
| 2010/0163242 A1 | 7/2010 | Dennis |
| 2012/0095686 A1 | 4/2012 | Legendre et al. |
| 2012/0293168 A1 | 11/2012 | Segletes et al. |
| 2013/0085685 A1 | 4/2013 | Linder et al. |
| 2013/0214786 A1 | 8/2013 | Hansen et al. |
| 2014/0200831 A1 | 7/2014 | Smith et al. |
| 2015/0066391 A1 | 3/2015 | Wang |
| 2015/0285607 A1* | 10/2015 | Helmore ............ E21B 47/02 33/558.2 |
| 2017/0284191 A1* | 10/2017 | Martin ............ E21B 47/12 |

OTHER PUBLICATIONS

Acuna, Irlec Alexandra, Et. Al., "Scanning for downhole corrosion," Oilfield Review, Spring 2010, pp. 42-50, vol. 22, No. 1, Schlumberger.

Rourke Marvin, Et. Al. "Multi-tubular corrosion inspection using a pulsed eddy current" IPTC 16645, Mar. 26-28, 2013, Beijing, China.

* cited by examiner

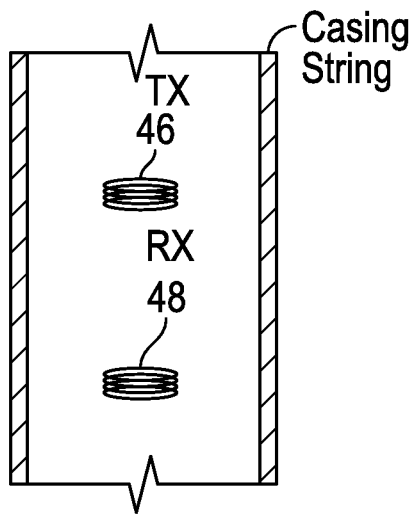
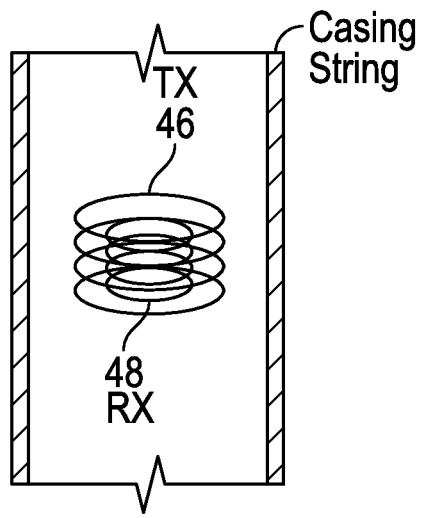
FIG. 2A  FIG. 2B
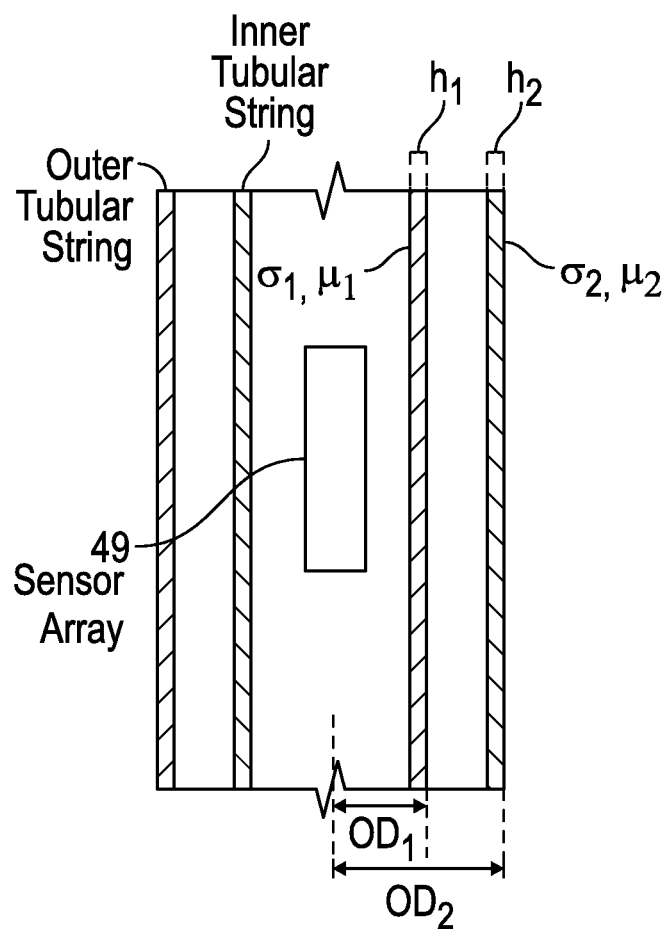
FIG. 3

ELECTROMAGNETIC (EM) DEFECT DETECTION METHODS AND SYSTEMS EMPLOYING DECONVOLVED RAW MEASUREMENTS

BACKGROUND

For oil and gas exploration and production, a network of wells installations and other conduits are established by connecting sections of metal pipe together. For example, a well installation may be completed, in part, by lowering multiple sections of metal pipe (i.e., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, corrosion transfer, etc. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data can be interpreted to correlate a level of flux leakage or EM induction with metal loss indicating corrosion. Obtaining meaningful EM field measurements and interpreting these measurements is an ongoing challenge, especially for multi-tubular scenarios. For example, a single defect can appear as two features in the measured response (referred to as a "ghost effect" herein). Efforts to improve the resolution of corrosion detection using EM logging are ongoing.

BRIEF DESCRIPTION OF THE DRAWINGS

Accordingly, there are disclosed in the drawings and the following description electromagnetic (EM) defect detection methods and systems employing deconvolved raw measurements. In the drawings:

FIGS. 2A and 2B are diagrams showing illustrative transmitter/receiver configurations for an EM defect detection tool for multi-string corrosion monitoring;

FIG. 3 is a diagram showing a multi-string model with related attributes;

Figure 1A:
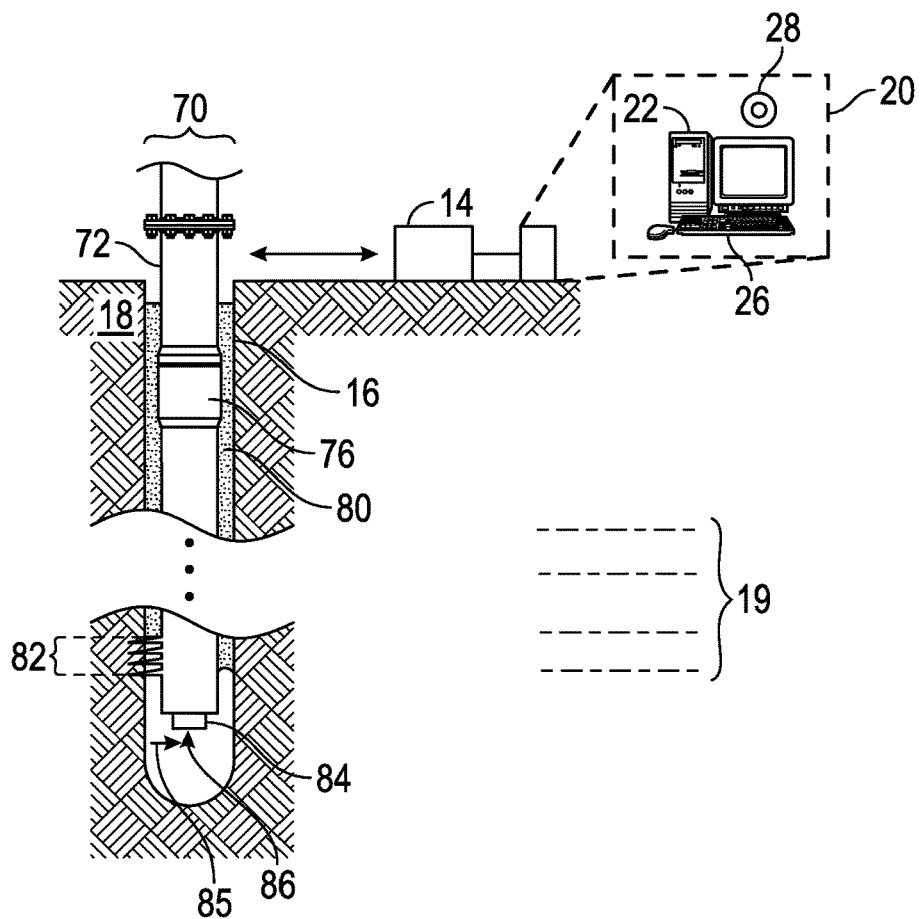
FIGS. 1A and 1B are diagrams showing illustrative multi-string survey environments.

It should be understood, however, that the specific embodiments given in the drawings and detailed description do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Disclosed herein are electromagnetic (EM) defect detection methods and systems employing deconvolved raw measurements. As used herein, "defect" refers to any type of metal loss or displacement such as thickness changes due to corrosion, holes, slots or any other deformation that results in a change in the material distribution of downhole pipes. In at least some embodiments, the disclosed methods and systems involve deployment of an EM defect detection tool in a downhole environment with a plurality of tubular strings. To detect defects in one or more of the plurality of tubular strings, the EM defect detection tool collects raw measurements for a plurality of transmitter/receiver spacings or frequencies. The collected raw measurements are deconvolved with an impulse response obtained, for example, from defect simulation and/or from previous measurements of a known defect. The output of the deconvolution is referred to herein as "deconvolved raw measurements." The deconvolved raw measurements may then be subject to filtering, scaling, and/or other operations, and the resulting values are then used to invert for defects in one or more tubular strings. One example inversion involves radial one-dimensional (R1D) processing. In an R1D inversion, the thickness of one or more tubular strings as a function of measured depth is determined. The thickness as a function of measured depth can be indicative of a defect (e.g., corrosion)

along a tubular string. As another example, EM properties of a tubular string as a function of measured depth may be determined, where the EM properties as a function of measured depth can be indicative of a defect along a tubular string.

In response to a determined defect, one or more operations can be performed by one or more devices. For example, an output device (e.g., a printer, computer monitor, tablet, etc.) may display a representation of any determined defects can be displayed using alphanumeric characters, geometric shapes and/or images. Additionally or alternatively, determined defects can be used to adjust downhole operations. For example, flow control devices (e.g., valves) in a well can be adjusted based on a determined defect. Additionally or alternatively, one or more devices that perform well intervention operations (e.g., to repair a tubular string in a well) can be deployed or initiated based on a determined defect. In different embodiments, the operations performed in response to the determine defect may include downhole operations and/or operations at earth's surface. The EM defect detection tool itself or components included with the EM defect detection tool may respond to a determined defect by performing one or more operations (e.g., telemetry operations or repair operations).

In at least some embodiments, an example method includes deploying an EM defect detection tool in a downhole environment having a plurality of tubing strings with different diameters. The method also includes receiving raw measurements collected by the EM defect detection tool, and deconvolving the raw measurements with another input to obtain deconvolved raw measurements. The method also includes using the deconvolved raw measurements to determine a defect in at least one of the plurality of tubular strings. The method also includes performing, by a device, an operation in response to the determined defect.

Meanwhile, in at least some embodiments, an example system includes an EM defect detection tool deployed in downhole environment having a plurality of tubing strings with different diameters. The system also includes a processing unit that deconvolves raw measurements collected by the EM defect detection tool with another input to obtain deconvolved raw measurements and that determines a defect in at least one of the plurality of tubular strings based at least in part on the deconvolved raw measurements. The system also includes a device that performs an operation in response to the determined defect. Various EM defect detection tool options, deconvolution options, measurement processing options, and defect response options are disclosed herein.

Figure 1B:
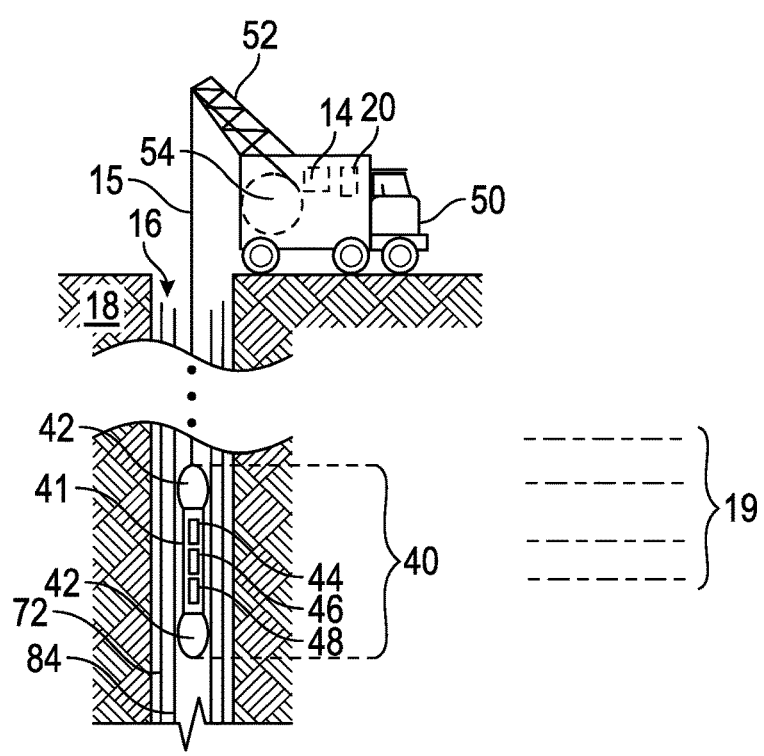

To provide some context for the disclosure, FIGS. 1A and 1B show illustrative multi-string survey environments. In FIG. 1A, a permanent well 70 is installed, for example, using a drilling rig to drill a borehole 16 that penetrates formations 19 of the earth 18. As shown, a casing string 72 is positioned in the borehole 16. The casing string 72 for well 70 includes multiple tubular casing sections (usually about 30 feet long) connected end-to-end by couplings 76. It should be noted that FIG. 1A is not to scale, and that casing string 72 typically includes many such couplings 76. The well 70 includes cement slurry 80 that has been injected into the annular space between the outer surface of the casing string 72 and the inner surface of the borehole 16 and allowed to set. As represented in FIG. 1A, a production tubing string 84 is positioned in an inner bore of the casing string 72. Both the casing string 72 and the production tubing string 84 are formed from multiple segments of metal pipe and are subject to corrosion.

In FIG. 1A, the well 70 corresponds to a production well and is adapted to guide a desired fluid (e.g., oil or gas) from a bottom of the borehole 16 to a surface of the earth 18. For example, perforations 82 may be formed at a bottom of or along the borehole 16 to facilitate the flow of a fluid 85 from a surrounding formation into the borehole 16 and thence to earth's surface via an opening 86 at the bottom of the production tubing string 84. Note that well configuration of FIG. 1A is illustrative and not limiting on the scope of the disclosure. Other examples of permanent well installations include injection wells and monitoring wells. As desired, well 70 may include other tubular strings in addition to or instead of casing string 72 and production tubing string 84.

In at least some embodiments, the well 70 may include a combination of tubular strings, perforations/screens, and flow control devices such that flow control to/from one or more downhole zones is possible. As desired, tubular defect detection using the techniques described herein can be used to adjust a flow control device for a particular zone (e.g., to reduce the amount of water in a produced fluid). Additionally or alternatively, tubular defect detection using the techniques described herein can be used to identify when/where well intervention operations are needed to repair a tubular string.

In the multi-string EM field survey environment of FIG. 1A, uplink or downlink information is transferred between an EM defect detection tool (see e.g., FIG. 1B) and a surface interface 14 and/or computer system 20. In some embodiments, the surface interface 14 and/or the computer system 20 may perform various operations such as converting signals from one format to another, storing EM log data collected by an EM logging tool, and/or processing EM log data to determine casing string attributes as described herein. In at least some embodiments, the computer system 20 includes a processing unit 22 that performs the EM log data analysis operations by executing software or instructions obtained from a local or remote non-transitory computer-readable medium 28. The computer system 20 also may include input device(s) 26 (e.g., a keyboard, mouse, touchpad, etc.) and output device(s) 24 (e.g., a monitor, printer, etc.). Such input device(s) 26 and/or output device(s) 24 provide a user interface that enables an operator to interact with an EM logging tool and/or software executed by the processing unit 22. For example, the computer system 20 may enable an operator to select analysis options, to view collected EM log data, to view analysis results, and/or to perform other tasks. While the computer system 20 is represented at earth's surface, another option is to perform some or all processing operations related to detecting a defect downhole (e.g., by processing units/components of an EM detect detection tool).

In different embodiments, an EM detect detection tool can be conveyed to a multi-string survey environment (e.g., the downhole environment of FIG. 1A) using wireline, slick line, coiled tubing, a casing string, wired pipe, or combinations thereof. For deployment options that do not provide power to the EM defect detection tool (e.g., powerless slick line, coiled tubing, or casing string), the EM defect detection tool may include a remote power source (e.g., a battery or other remote power source) to power the antennas or other electronics.

FIG. 1B illustrates a wireline logging environment in which an EM defect detection tool 40 is positioned within production tubing string 84 and casing string 72. In FIG. 1B, the EM defect detection tool 40 is suspended in borehole 16 that penetrates formations 19 of the earth 18. For example, the EM defect detection tool 40 may be suspended by a cable 15 having conductors and/or optical fibers for conveying power to the EM defect detection tool 40. The cable 15 may also be used as a communication interface for uplink and/or downlink communications. In at least some embodiments, the cable 15 wraps and unwraps as needed around cable reel 54 when lowering or raising the EM defect detection tool 40. As shown, the cable reel 54 may be part of a movable logging facility or vehicle 50 having a cable guide 52. Other conveyance options (e.g., slick line, coiled tubing, a casing string, wired pipe, or combinations) may use other techniques and components to convey the EM defect detection tool 40 along a multi-tubular survey environment.

The EM defect detection tool 40 may include stabilizers 42 on one or more ends (e.g. opposite ends) of a tool body 41 to centralize the EM defect detection tool 40 within the production tubing string 84. The tool body 41 of the EM logging tool 40 houses or provides a support structure for control electronics 44, transmitter(s) 46, and receiver(s) 48. In operation, transmitter(s) 46 are directed by the control electronics 44 to generate a time-varying EM field whose flux is guided by the production tubing string 84 and/or casing string 72. Due to induced eddy currents, the flux guide provided by the production tubing string 84 and/or casing string 72 is lossy, but will still induce a voltage in receiver(s) 48. The control electronics 44 stores the voltages recorded by receiver(s) 48 to form an EM data log, which may be correlated with geometrical, electrical, and/or magnetic attributes of the production tubing string 84 and/or casing string 72. For example, corrosion or other defects in the production tubing string 84 and/or casing string 72 affects their geometrical, electrical, and/or magnetic attributes and can therefore be estimated from analysis of the EM log data. The control electronics 44 may also include a communication interface to transmit the EM data log to earth's surface. Additionally or alternatively, the EM data log obtained by the EM defect detection tool 40 can be stored and accessed later once the tool 40 reaches earth's surface.

At earth's surface, the surface interface 14 receives the EM data log via the cable 15 and conveys the EM field measurements to a computer system 20. Again, the interface 14 and/or computer system 20 (e.g., part of the movable logging facility or vehicle 50) may perform various operations such as converting signals from one format to another, storing the EM log data, and/or analyzing the EM log data to determine casing string attributes.

FIGS. 2A and 2B show illustrative transmitter/receiver configurations for an EM defect detection tool (e.g., tool 40). In FIG. 2A, transmitter 46 and receiver 48 are positioned within a casing string (e.g., strings 72 or 84) and are separated. Meanwhile, in FIG. 2B, transmitter 46 and receiver 48 are positioned within a casing string (e.g., strings 72 or 84) and are collocated. For example, transmitter 46 and receiver 48 may correspond to coils or solenoids, where the receiver 48 is positioned inside the transmitter 46, or vice versa. While only one transmitter 46 and one receiver 48 are shown in FIGS. 2A and 2B it should be understood, that EM defect detection tools such as tool 40 may have a plurality of sensor arrays, where the distance between transmitters 46 and receivers 48 for different sensor arrays may vary. The dimensions or other characteristics (e.g., number of windings, diameter of windings, etc.) of the transmitters 46 and receivers 48 may vary for different sensor arrays. Also, the operation of each sensor array may be varied by frequency-domain or time-domain adjustments.

FIG. 3 shows a multi-string model with related attributes. In FIG. 3, a sensor array 49 (e.g., one or more transmitter/receiver arrays) is positioned within two casing strings (inner and outer casing strings). The sensing array 49 may be part of an EM defect detection tool such as tool 40 to enable various attributes (e.g., tubular wall thickness, conductivity, permeability) of the inner and outer casing strings to be estimated. In the example multi-string scenarios of FIGS. 1A and 1B, the casing string 72 is an outer tubular string, while the production tubing string 84 is an inner tubular string.

In at least some embodiments, a one-dimensional radial (R1D) inversion model and R1D processing may be used to calculate multi-string casing attributes. The R1D processing may be performed downhole and/or at earth's surface. As an example, attributes that may be calculated for the multi-string model of FIG. 3 include inner tubular outer diameter ($OD_1$), inner tubular thickness ($h_1$), inner tubular conductivity ($\sigma_1$), inner tubular permeability ($\mu_1$), outer tubular diameter ($OD_2$), outer tubular thickness ($h_2$), outer tubular conductivity ($\sigma_2$), and outer tubular permeability ($\mu_2$). While only two tubular strings are shown in the multi-string model of FIG. 3, it should be noted that EM log data and multi-string models can be used to determine attributes for more than two tubular strings.

Figure 4:
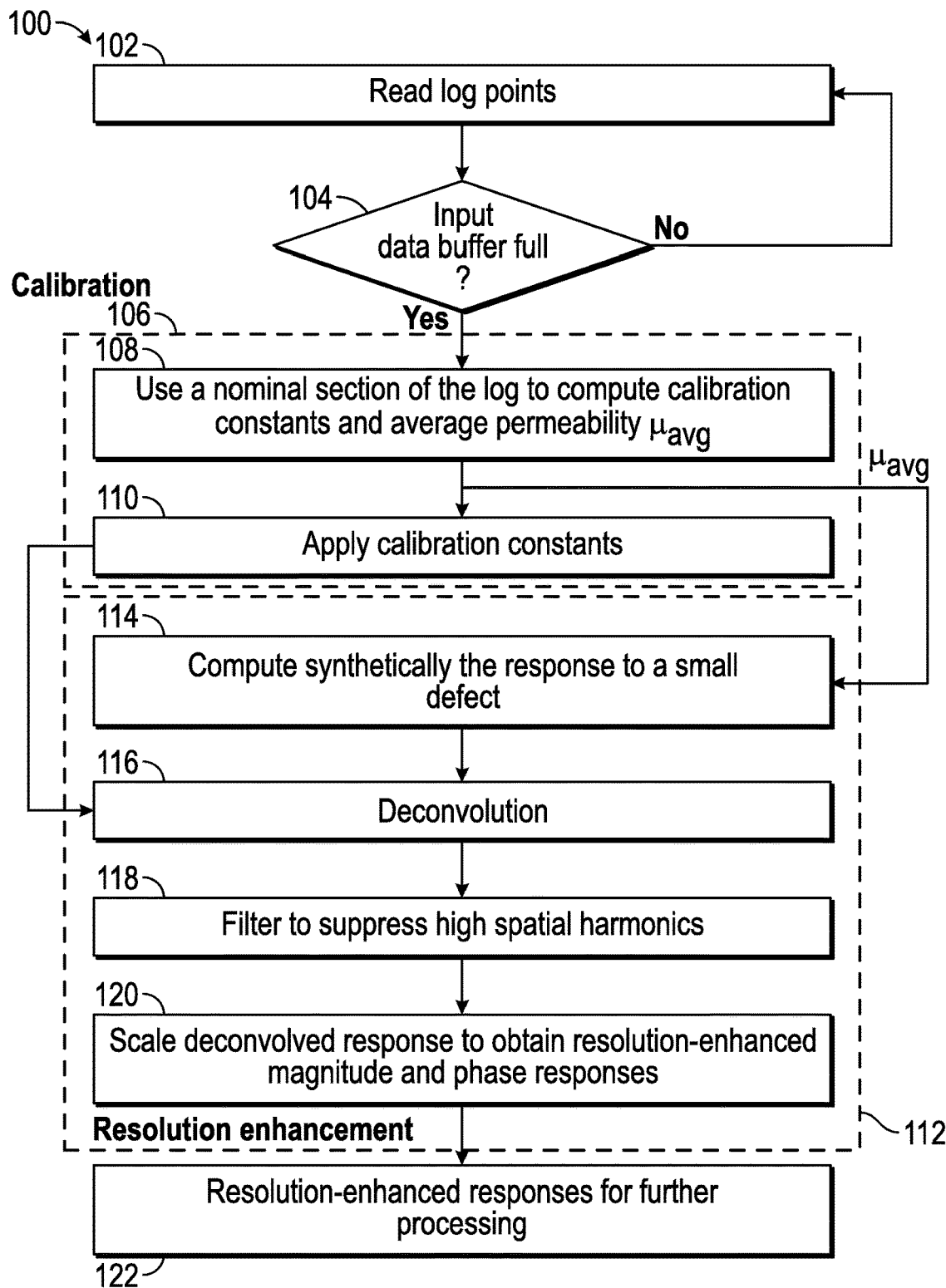
FIG. 4 is a flowchart showing an illustrative method for EM defect detection for downhole tubulars.

FIG. 4 is a flowchart showing an illustrative method 100 for EM defect detection for downhole tubulars. In method 100, EM log data points (raw measurements) are read at block 102. The raw measurements are collected, for example, by the EM defect detection tool while deployed in a downhole environment having a plurality of tubing strings with different diameters. If the input data buffer that stores the raw measurements is not full (decision block 104), the method 100 returns to block 102. Once the input data buffer is full (decision block 104), the method 100 proceeds to a calibration process 106 that includes using a nominal section of the log to compute calibration constants and average permeability ($\mu_{avg}$) at block 108. At block 110, the calibration constants are applied. In different embodiments, the calibration process 106 can be omitted or modified.

After the calibration process 106, the method 100 proceeds to a resolution-enhancement process 112 that includes deconvolution at block 116. The inputs to the deconvolution process of block 116 includes calibrated raw measurements and an impulse response obtained from block 114, where the impulse response is computed synthetically by modeling an EM defect detection tool response to a representative defect. The dimensions of the representative defect should be small enough to mimic an impulse, but not too small (to avoid numerical errors). In at least some embodiments, the impulse response is computed at block 114 using the value for $\mu_{avg}$ obtained at block 108. In alternative embodiments, the impulse response used for the deconvolution process of block 116 is obtained by measuring the EM defect detection tool response to a known defect in a tubular (e.g., in a test or laboratory environment). The modeled or measured defect can have any arbitrary shape with its length being as small as possible along the axial direction while still enabling an accurate measurement with an EM defect detection tool. To build a synthetic model, the geometry of tubulars (e.g., the number of tubulars, the outer diameters of tubulars, and the nominal thickness of tubulars) as well as their electrical and magnetic properties need to be known or selected. For a given well, the number of tubulars, the outer diameters of tubulars, and the nominal thickness of tubulars are usually known a priori. The magnetic permeabilities of the tubulars, however, are not precisely known and can vary a lot from one casing segment to another. Accordingly, the average permeability estimated from the calibration process may be used as the permeability of all tubulars in the synthetic model. If multiple defects are detected on multiple tubulars, then for each measurement (receiver/frequency combination) the tubular to which that measurement is most sensitive is picked for impulse response computation. For example, in a scenario with four tubular strings and EM defect detection tool with six receivers, the impulse response of the inner tubulars (tubulars 1 or 2) can be used to deconvolve receivers 1, 2, and 3, while the impulse response of the outer tubular (tubulars 3 or 4) can be used to deconvolve receivers 4, 5, and 6. This approach can be directly used without having to detect which pipe has a defect beforehand.

As previously mentioned, the computed or obtained impulse response is provided as an input for the deconvolution performed of block 116, which may involve the following process. For each receiver i and frequency j, the Fourier transform is applied to convert the complex-valued measured response $m_{i,j}(z)$, which is a function of depth z, into the spatial harmonics of the response as a function of the spatial frequency k in cycles per foot (cpf) $M_{i,j}(k)$. The deconvolved response in the spatial frequency domain $D_{i,j}(k)$ is computed as:

$$D_{i,j}(k) = \frac{M_{i,j}(k)}{H_{i,j}(k)}, \qquad \text{Equation (1)}$$

where $H_{i,j}(k)$ is the impulse response of receiver i and frequency j in the spatial frequency domain. A simple division as in Equation (1) may amplify the noise at high spatial frequencies, rendering the deconvolved signal noisy when transformed back into the spatial domain. Accordingly, in at least some embodiments, the resolution-enhancement process 112 applies filtering to the deconvolved raw measurements at block 118 to suppress high-spatial harmonics. As an example, the filtered response in the spatial frequency domain may be given as:

$$R_{i,j}(k) = F(k) \times D_{i,j}(k), \qquad \text{Equation (2)}$$

where F(k) can be any appropriately designed low pass filter such that it reduces the spurious high frequency components while keeping the useful high frequency content of the signal as intact as possible. An Inverse Fourier transform is applied to convert $R_{i,j}(k)$ into a spatial domain response, $r_{i,j}(z)$, which has higher resolution (compared to the raw response) and is free from ghosts. In at least some embodiments $r_{i,j}(z)$ reaches the resolution limit of the tool, which is determined by the geometry of the transmitters/receivers and the signal-to-noise ratio (SNR) the data was acquired with.

The resolution-enhancement process 112 may also scale the deconvolved raw measurements at block 120 to obtain resolution-enhanced magnitude and phase responses. In at least some embodiments, the spatial domain response, $r_{i,j}(z)$, is scaled and level shifted before it can be used as a resolution-enhanced surrogate for the raw response $m_{i,j}(z)$. For example, the scaling and level shifting can be performed according to:

$$\hat{m}_{i,j}(z) = \qquad \text{Equation (3)}$$
$$(r_{i,j}(z) - r_{i,j}(z_{nom})) \times \frac{m_{i,j}(z_{peak,m}) - m_{i,j}(z_{nom})}{r_{i,j}(z_{peak,r}) - r_{i,j}(z_{nom})} + m_{i,j}(z_{nom}),$$

where $\hat{m}_{i,j}(z)$ is the resolution-enhanced response, and where $m_{i,j}(z_{nom})$ and $r_{i,j}(z_{nom})$ are the responses at a nominal (non-defected) section. This nominal section can be identified by inspecting the responses and identifying sections with minimum variations or by averaging out a long enough log to minimize the effect of any present defect. In Equation (3), $z_{peak,m}$ is given as:

$$z_{peak,m} = \mathrm{argmax}_z(\mathrm{abs}(m_{i,j}(z) - m_{i,j}(z_{nom}))). \qquad \text{Equation (4)}$$

Meanwhile, $z_{peak,r}$ in Equation (3) is given as:

$$z_{peak,r} = \mathrm{argmax}_z(\mathrm{abs}(r_{i,j}(z) - r_{i,j}(z_{nom}))). \qquad \text{Equation (5)}$$

For the resolution-enhancement process 112, the calculations related to Equations (1) to (5) are repeated for all receivers and frequencies. As an option, if the noise spectrum and error ranges in the collected measurements are known or can be estimated beforehand or during the method 100, Wiener filtering may be used to perform the inverse filtering in Equation (1).

The output of the resolution-enhancement process 112 is further processed at block 122 to determine defects in one or more tubulars. For example, the output from the resolution-enhancement process 112 can be inverted to determine thickness, relative permeability, and/or conductivity values for one or more positions along a tubular string or along multiple tubular strings. The thickness, relative permeability, and/or conductivity values can be correlated with tubular defects such as corrosion. As needed, the results of performing method 100 can be used to display a representation of determined defects and/or to adjust valves or other flow control devices for one or more zones of a production well (e.g., well 70). Additionally or alternatively, well intervention operations may be performed (to repair or alter flow paths in the well) based on the results of performing method 100 based on raw measurements collected at one or more axial positions of a downhole environment having a plurality of tubular strings with different diameters.

Figure 5:
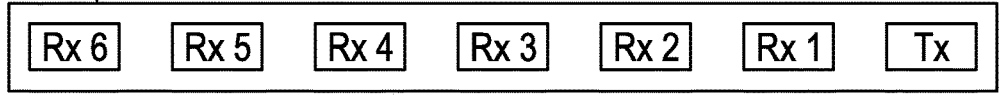
FIG. 5 is a block diagram of an illustrative EM defect detection tool.

Hereafter, various EM defect detection scenarios are presented. The scenarios described are examples only and are not intended to limit EM defect detection to a particular EM defect detection tool or scenario. FIG. 5 is a block diagram of an illustrative EM defect detection tool 40A having a transmitter (Tx) and six spaced receivers (Rx1-Rx6). Although the EM defect detection tool 40A is represented in the EM defect detection scenarios given hereafter, it should be appreciated that EM defect detection tools may vary with regard to the number of transmitters, the number of receivers, the transmitter/receiver spacings, and the frequencies used. As desired, collocated transmitter/receiver options are possible.

Figures 6A, 6B:
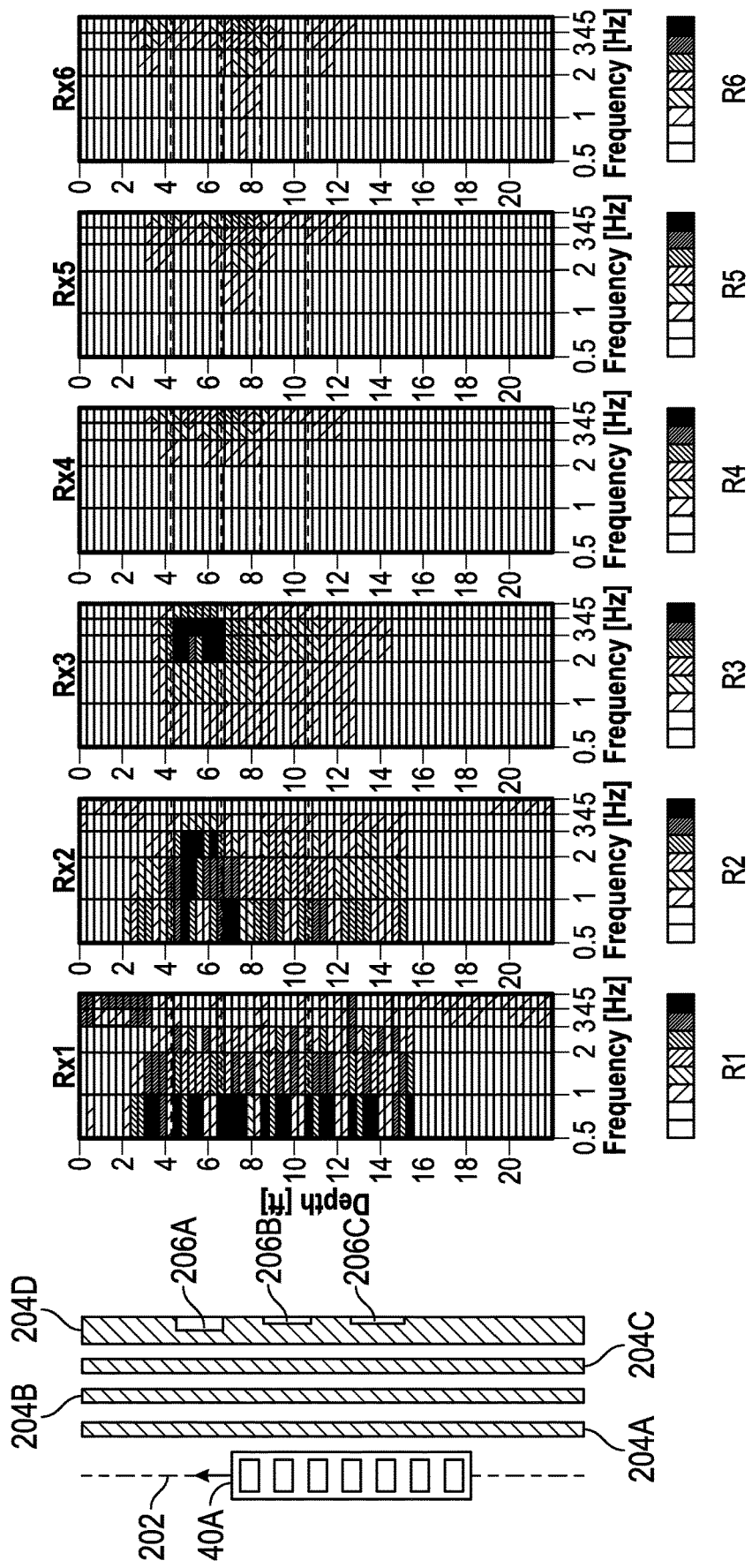
FIG. 6A is a diagram showing an illustrative first EM defect detection scenario.
FIG. 6B is a diagram showing raw magnitude responses for different receivers in the first EM defect detection scenario.

FIG. 6A is a diagram showing an illustrative first EM defect detection scenario and related raw magnitude responses (without deconvolution) for different receivers. As shown in FIG. 6A, the first EM defect detection scenario corresponds to the EM defect detection tool 40A being deployed in a downhole environment with four tubular strings 204A-204D having different diameters (only a slice of the four tubular strings 204A-204D is shown). Parameters of the tubulars used in the first EM defect detection scenario are summarized in Table 1.

TABLE 1

| Tubular | 204A | 204B | 204C | 204D |
|---|---|---|---|---|
| OD (inches) | 2.875 | 5 | 9.625 | 13.375 |

TABLE 1-continued

| Tubular | 204A | 204B | 204C | 204D |
|---|---|---|---|---|
| Thickness (inches) | 0.217 | 0.625 | .545 | 0.514 |
| Relative μ (estimate) | 62 | 60 | 58 | 82 |
| Length (feet) | 20 | 20 | 20 | 20 |
| Defect(s) | None | None | None | 0.09 inches × 2 feet, centered at 5 ft (17.5%) 0.05 inches × 2 feet, centered at 9 ft (10%) 0.03 inches × 2 feet, centered at 13 ft (6%) |

For the first EM defect detection scenario, thickness defects are present in the tubular string 204D. As the EM defect detection tool 40A moves axially along measurement path 202, raw measurements are collected by the EM detect detection tool 40A. For the example given, the EM detect detection tool 40A operates at frequencies ranging from 0.5 Hz to 5 Hz.

FIG. 6B shows an illustrative raw magnitude measurements corresponding to receivers Rx1-Rx6 as a function of axial position along the measurement path 202. In at least some embodiments, the raw magnitude measurements are associated with different frequency ranges (R1-R6), where the frequency ranges may or may not overlap. It should be appreciated that the frequency ranges used for EM defect detection may vary for different EM defect detection tools or scenarios.

Figure 7:
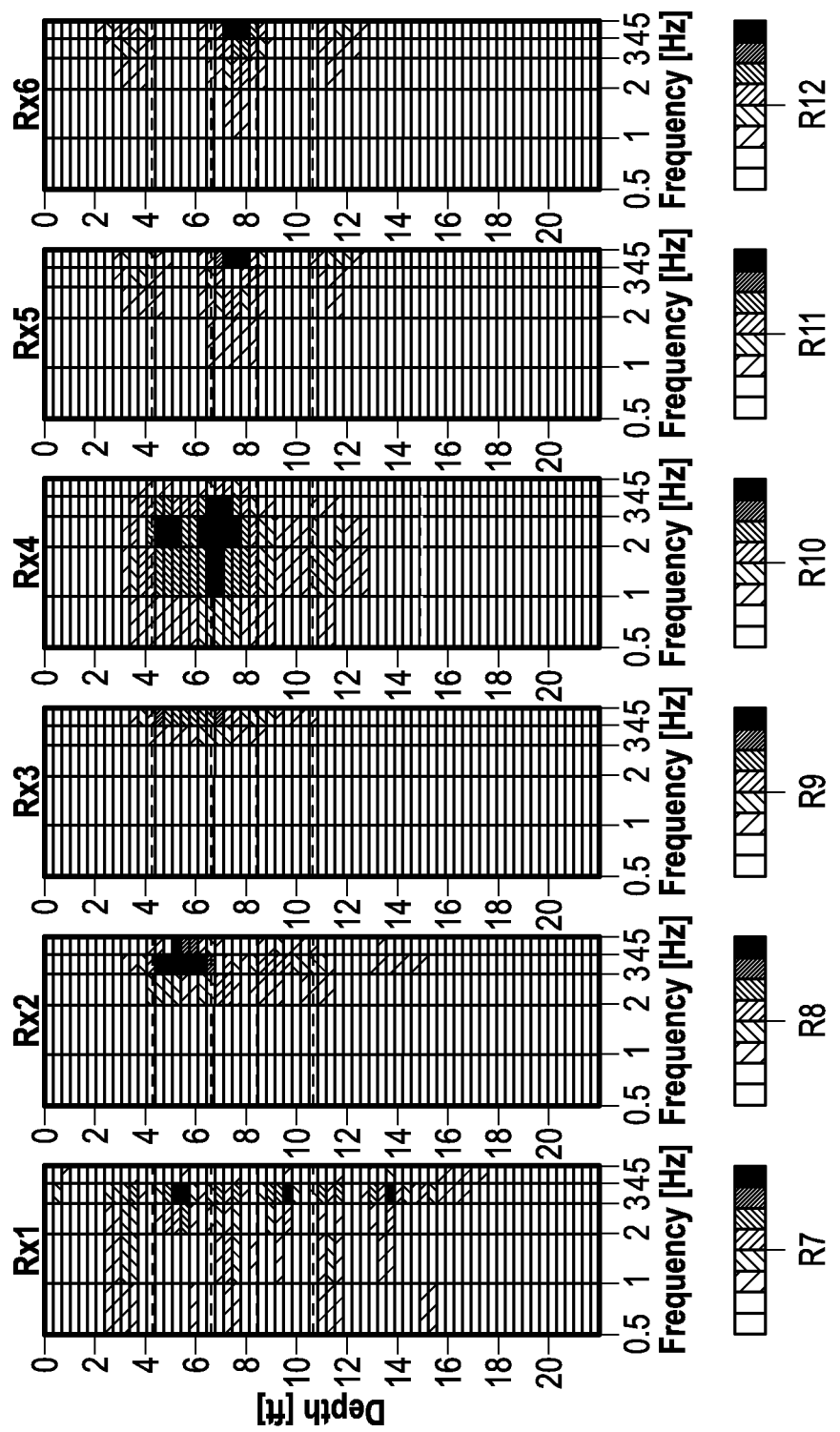
FIG. 7 is a diagram showing raw phase responses for different receivers in the first EM defect detection scenario.

FIG. 7 is a diagram showing raw phase responses (without deconvolution) for different receivers in the first EM defect detection scenario. The raw phase measurements correspond to receivers Rx1-Rx6 as a function of axial position along the measurement path 202 (see FIG. 6A). In at least some embodiments, the raw phase measurements are associated with different frequency ranges (R7-R12), where the frequency ranges may or may not overlap. Again, frequency ranges used for EM defect detection may vary for different EM defect detection tools or scenarios. In FIGS. 6B and 7, the raw measurement responses of the long spacing receivers (e.g., Rx4 through Rx6) are not aligned with the actual defects due to the ghosting effect. To improve defect detection, deconvolution and other resolution-enhancement techniques (e.g., the resolution-enhancement process 112) may be applied as described herein.

Figure 8A:
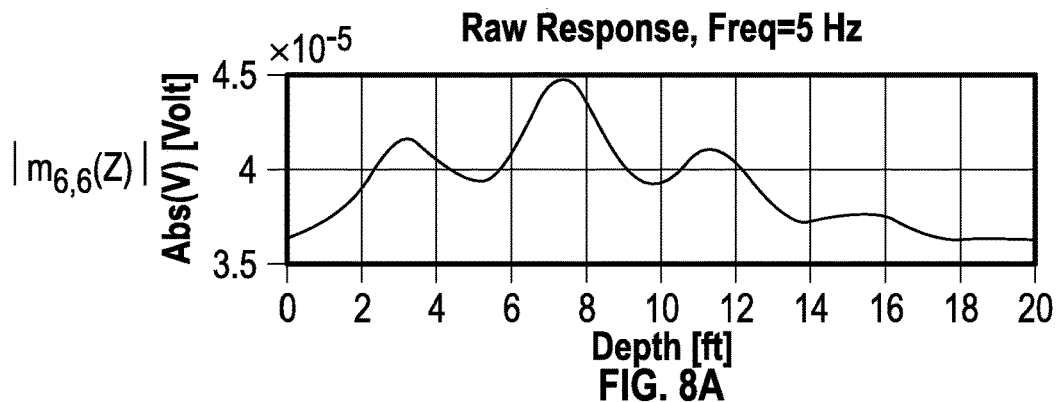
FIGS. 8A-8H is a diagram showing illustrative response charts related to the first EM defect detection scenario.
Figure 8B:
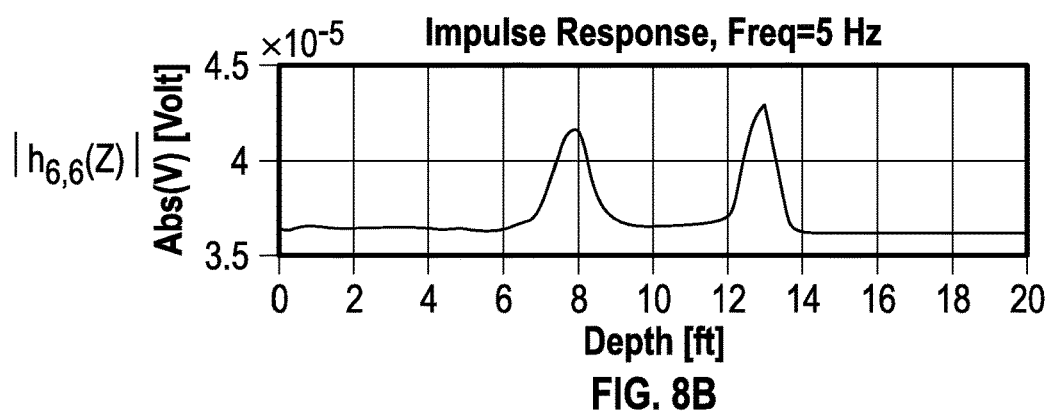
Figure 8C:
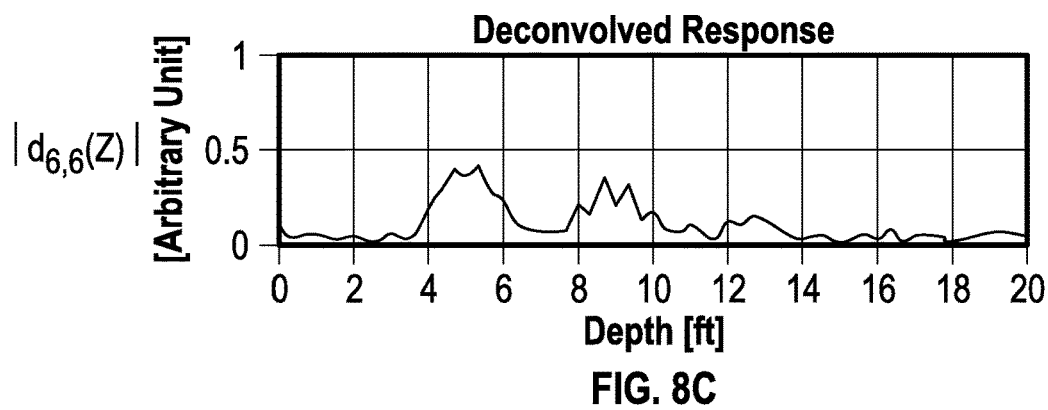
Figure 8D:
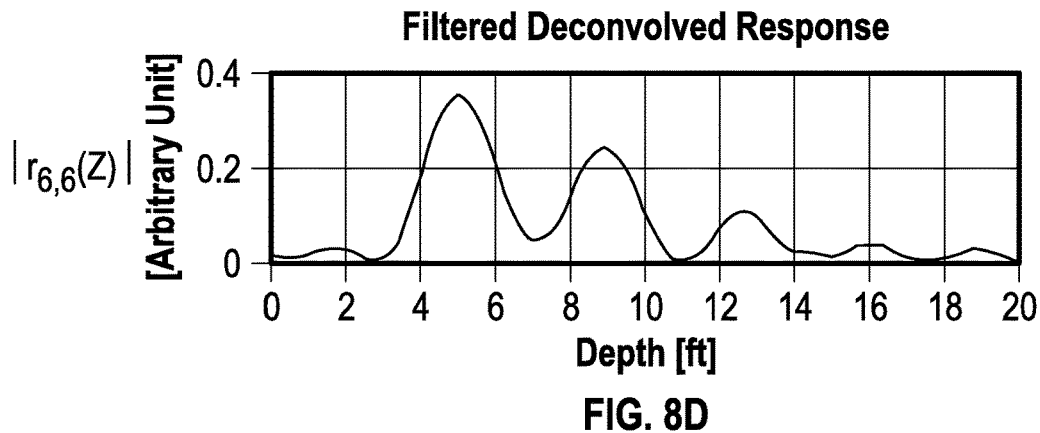
Figure 8E:
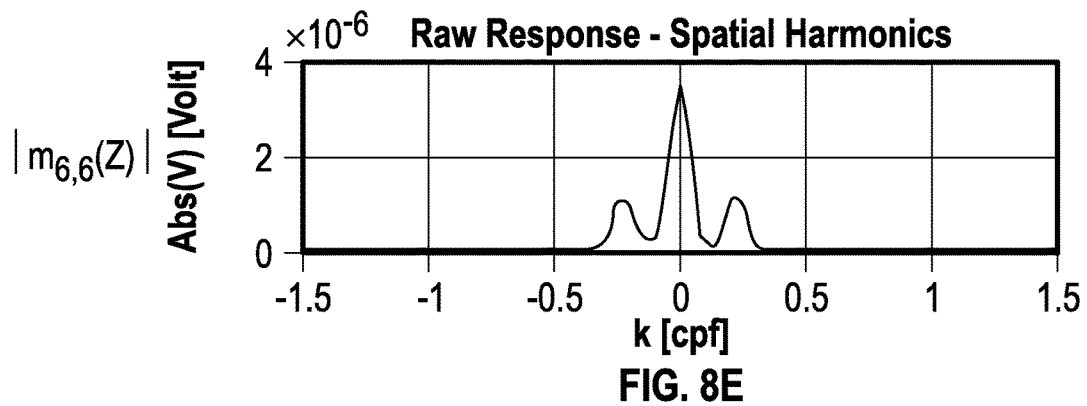
Figure 8F:
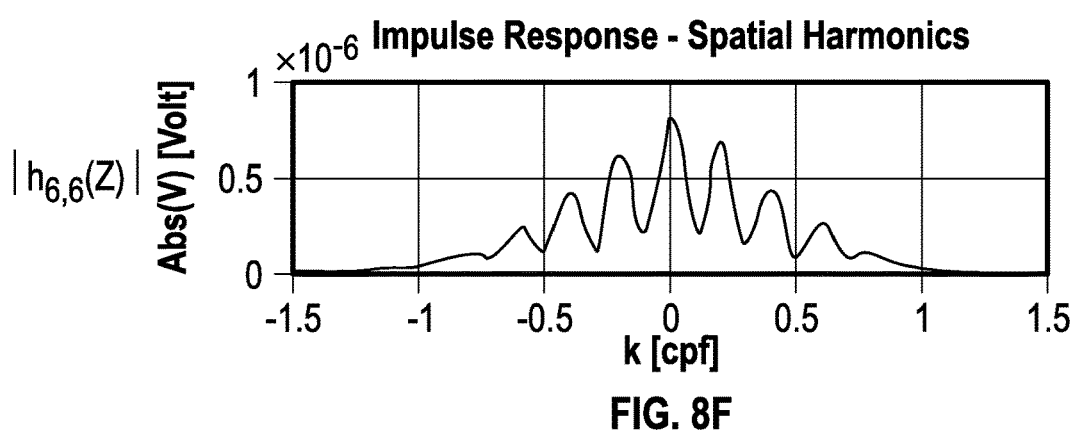
Figure 8G:
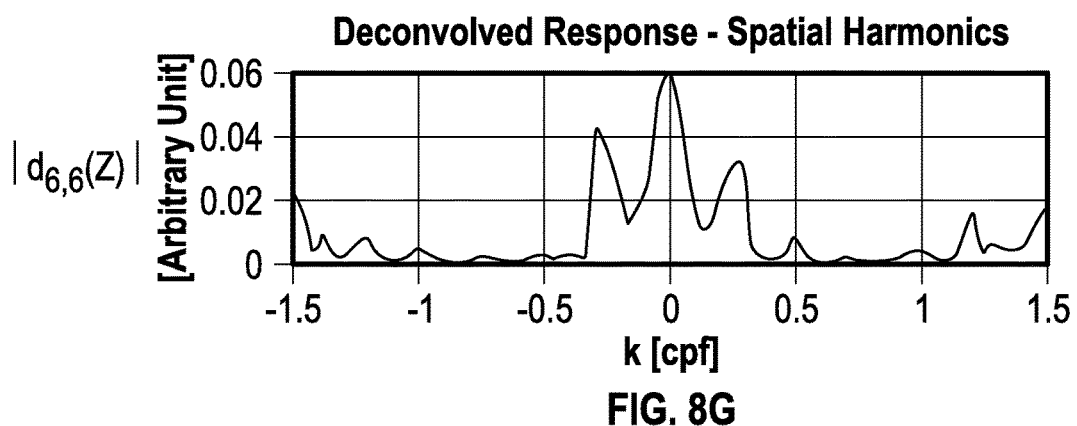
Figure 8H:
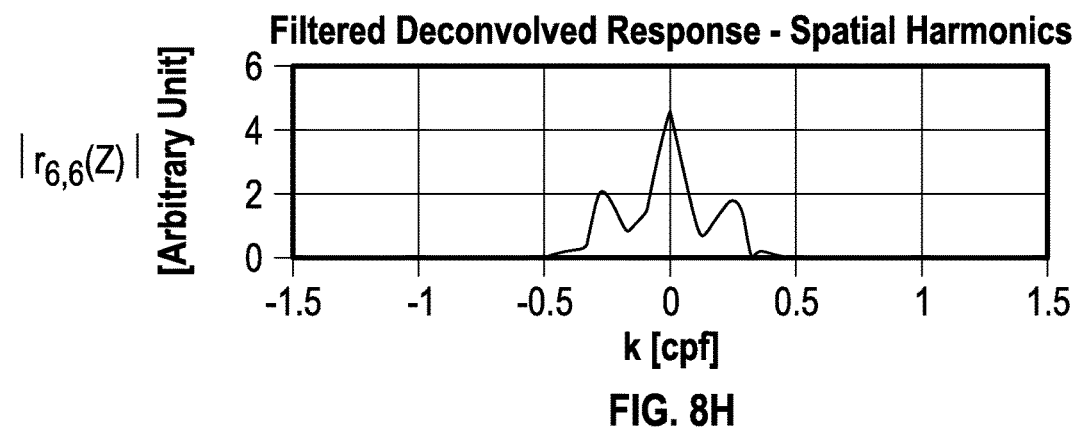

FIGS. 8A-8H are diagrams showing illustrative response charts related to the first EM defect detection scenario. More specifically, the response charts of FIGS. 8A-8H correspond to a particular receiver (receiver 6 or Rx6) and frequency (frequency 6—e.g., 5 Hz). For other receivers, frequencies, and defect detection scenarios, the responses would vary. FIG. 8A shows the raw response for the given receiver and frequency (i.e., $|m_{6,6}(z)|$), FIG. 8B shows the impulse response for the given receiver and frequency (i.e., $|h_{6,6}(z)|$), FIG. 8C shows the deconvolved response for the given receiver and frequency (i.e., $|d_{6,6}(z)|$), and FIG. 8D shows the filtered deconvolved response for the given receiver and frequency (i.e., $|r_{6,6}(z)|$). Meanwhile, FIG. 8E shows the spatial harmonics of the raw response for the given receiver and frequency (i.e., $|M_{6,6}(z)|$), FIG. 8F shows the spatial harmonics of the impulse response for the given receiver and frequency (i.e., $|H_{6,6}(z)|$), FIG. 8G shows the spatial harmonics of the deconvolved response for the given receiver and frequency (i.e., $|D_{6,6}(z)|$), and FIG. 8H shows the spatial harmonics of the deconvolved response for the given receiver and frequency (i.e., $|R_{6,6}(z)|$).

Figure 9A:
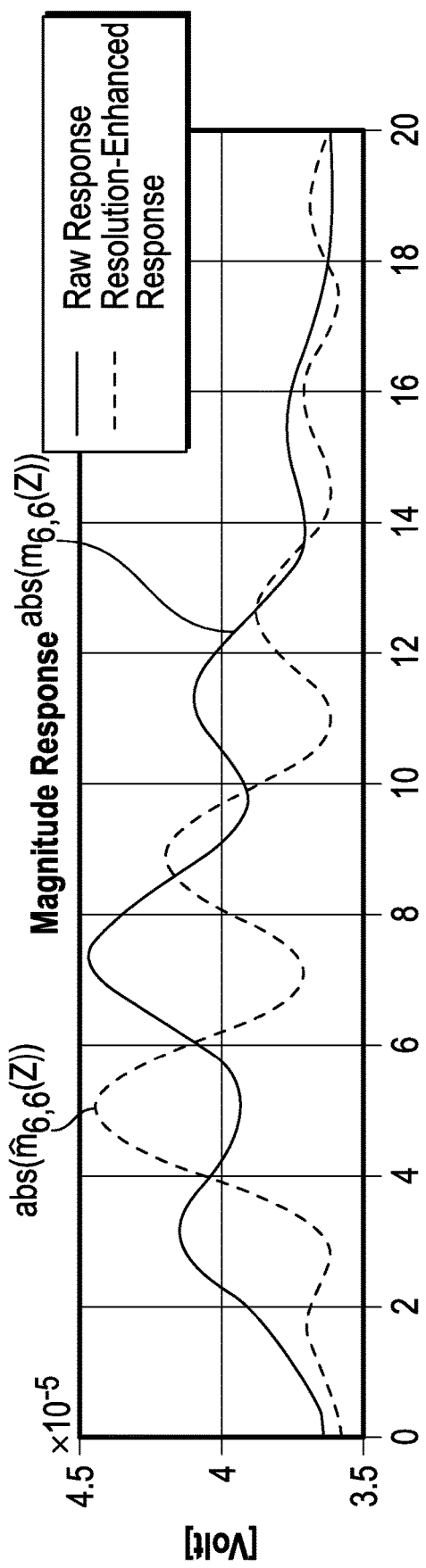
FIGS. 9A and 9B are diagrams showing response charts comparing EM defect detection with and without deconvolved raw measurements.
Figure 9B:
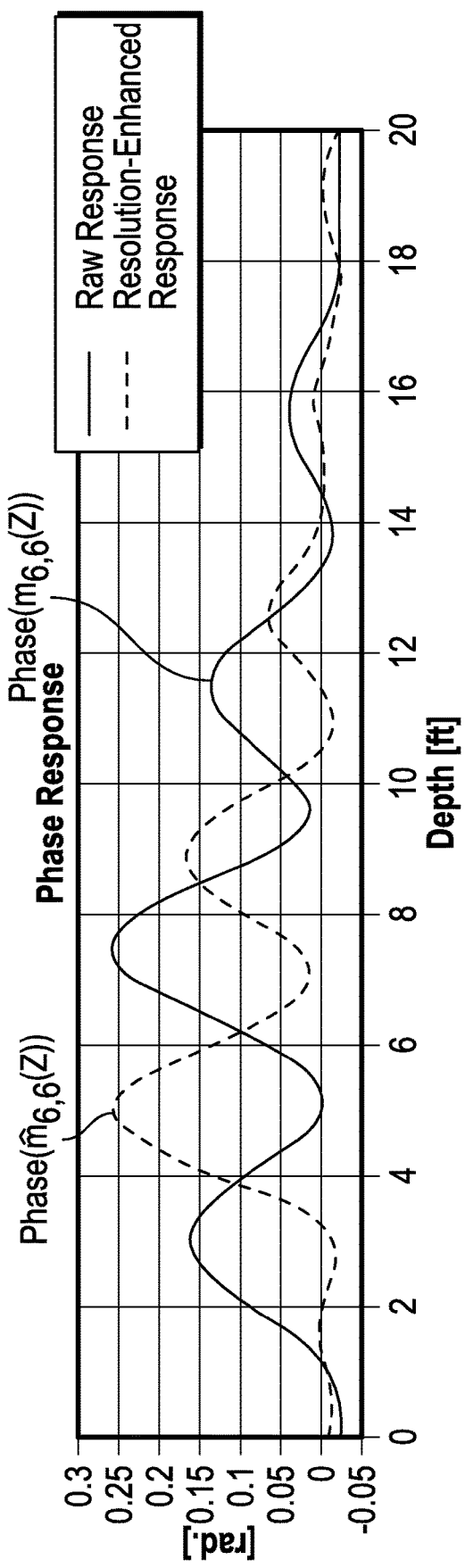

FIGS. 9A and 9B are diagrams showing additional response charts comparing EM defect detection with and without deconvolved raw measurements. Similar to the response charts of FIGS. 8A-8H, the response charts of FIGS. 9A and 9B correspond to a particular receiver (receiver 6 or Rx6) and frequency (frequency 6—e.g., 5 Hz). As shown in FIGS. 9A and 9B, both the resolution-enhanced magnitude response and the resolution-enhanced phase response (e.g., the output of process 112) are shifted compared to the original raw responses, resulting in more accurate defect detection.

Figure 10:
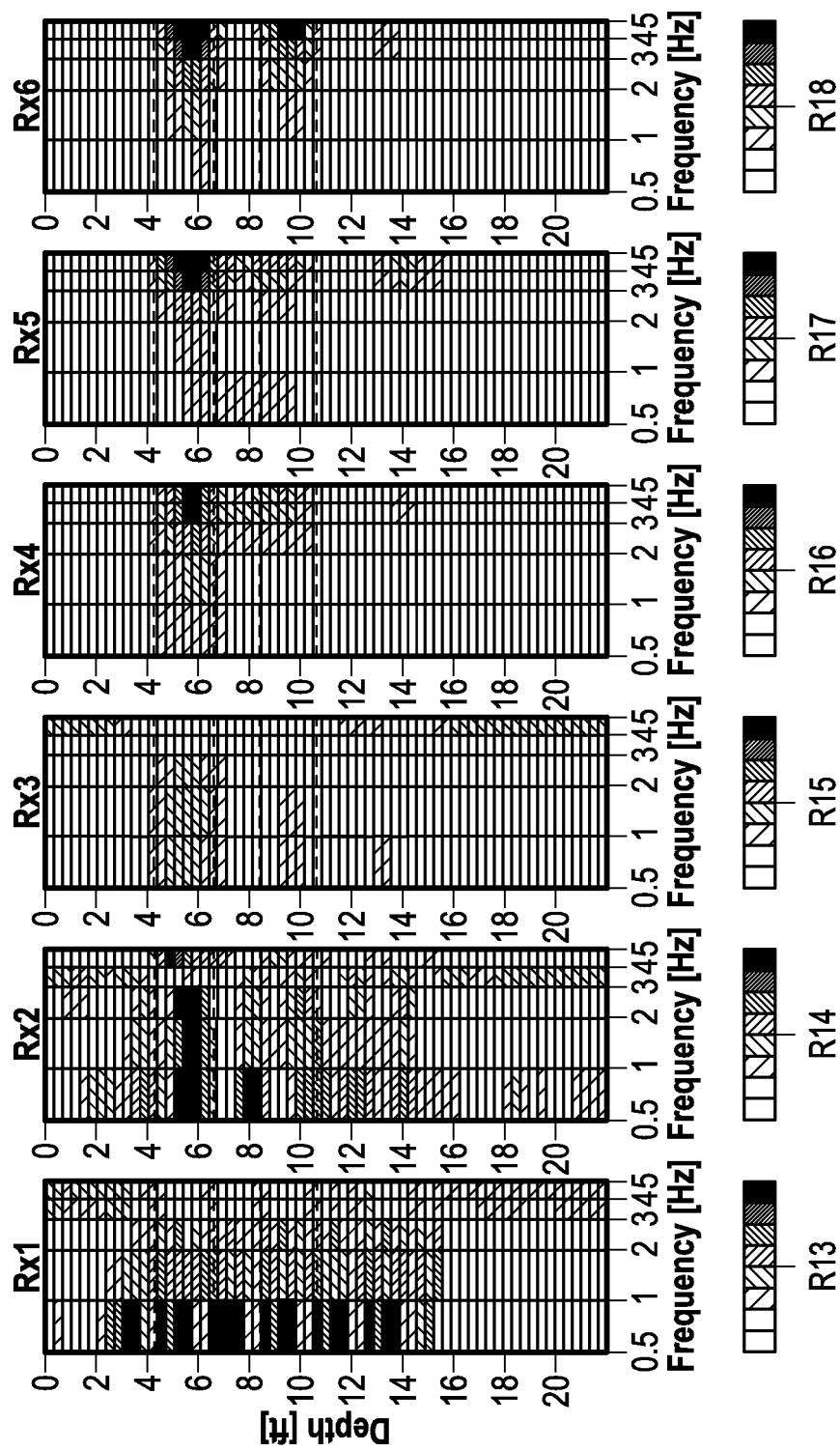
FIG. 10 is a diagram showing deconvolved raw magnitude responses for different receivers in the first EM defect detection scenario.

FIG. 10 is a diagram showing deconvolved raw magnitude responses for different receivers in the first defect detection scenario. The deconvolved raw magnitude responses correspond to each of the receivers Rx1-Rx6 as a function of axial position along the measurement path 202. In at least some embodiments, the deconvolved raw magnitude responses are associated with different frequency ranges (R13-R18), where the frequency ranges may or may not overlap. The deconvolved raw magnitude responses may be obtained, for example, using the resolution-enhancement process 112 described previously.

Figure 11:
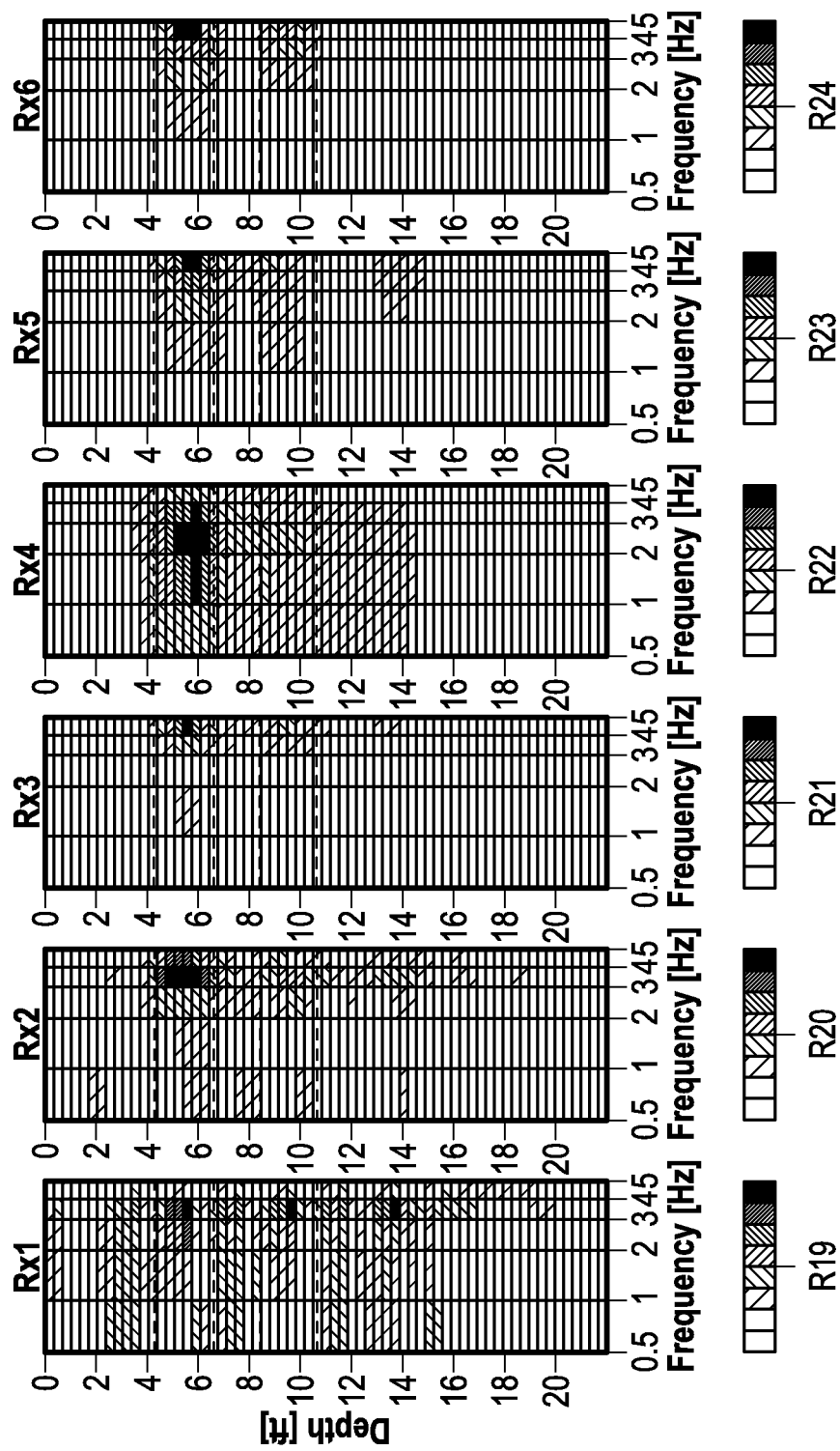
FIG. 11 is a diagram showing deconvolved raw phase responses for different receivers in the first EM defect detection scenario.

FIG. 11 is a diagram showing deconvolved raw phase responses for different receivers in the first defect detection scenario. The deconvolved raw phase responses correspond to receivers Rx1-Rx6 as a function of axial position along the measurement path 202. In at least some embodiments, the deconvolved raw phase responses are associated with different frequency ranges (R19-R24), where the frequency ranges may or may not overlap. The deconvolved raw phase responses may be obtained, for example, using the resolution-enhancement process 112 described previously. In FIGS. 10 and 11, the deconvolved raw measurements of the long spacing receivers (e.g., Rx4 through Rx6) are aligned with the actual defects, and can thus improve defect detection as described herein.

Figure 12A:
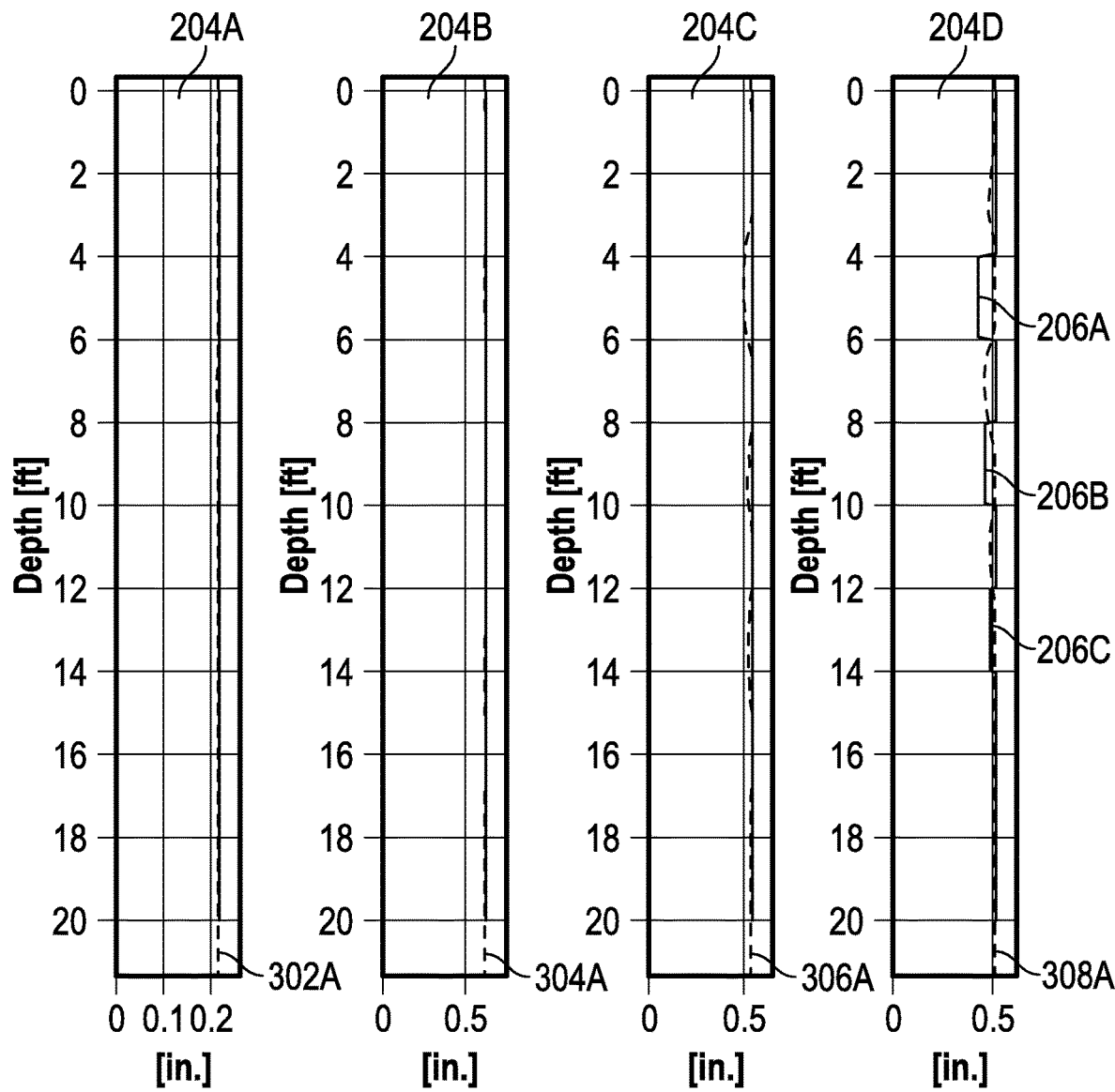
FIG. 12A is a diagram showing actual and predicted defects for the first EM defect detection scenario without deconvolved raw measurements.

FIG. 12A is a diagram showing actual and predicted defects for the first EM defect detection scenario without deconvolved raw measurements. In FIG. 12A, the predicted thickness lines 302A, 304A, 306A, and 308A are based on raw measurements (without deconvolution) and result in errors with regard to both the tubular(s) at issue and the defect locations along the tubular(s) relative to the actual defects 206A-206C. In particular, the predicted thickness line 306A incorrectly indicates that there are thickness variations along tubular 204C. Meanwhile, the predicted thickness line 308A correctly indicates that there are thickness variations along tubular 204D, but the location of the thickness variations are incorrect.

Figure 12B:
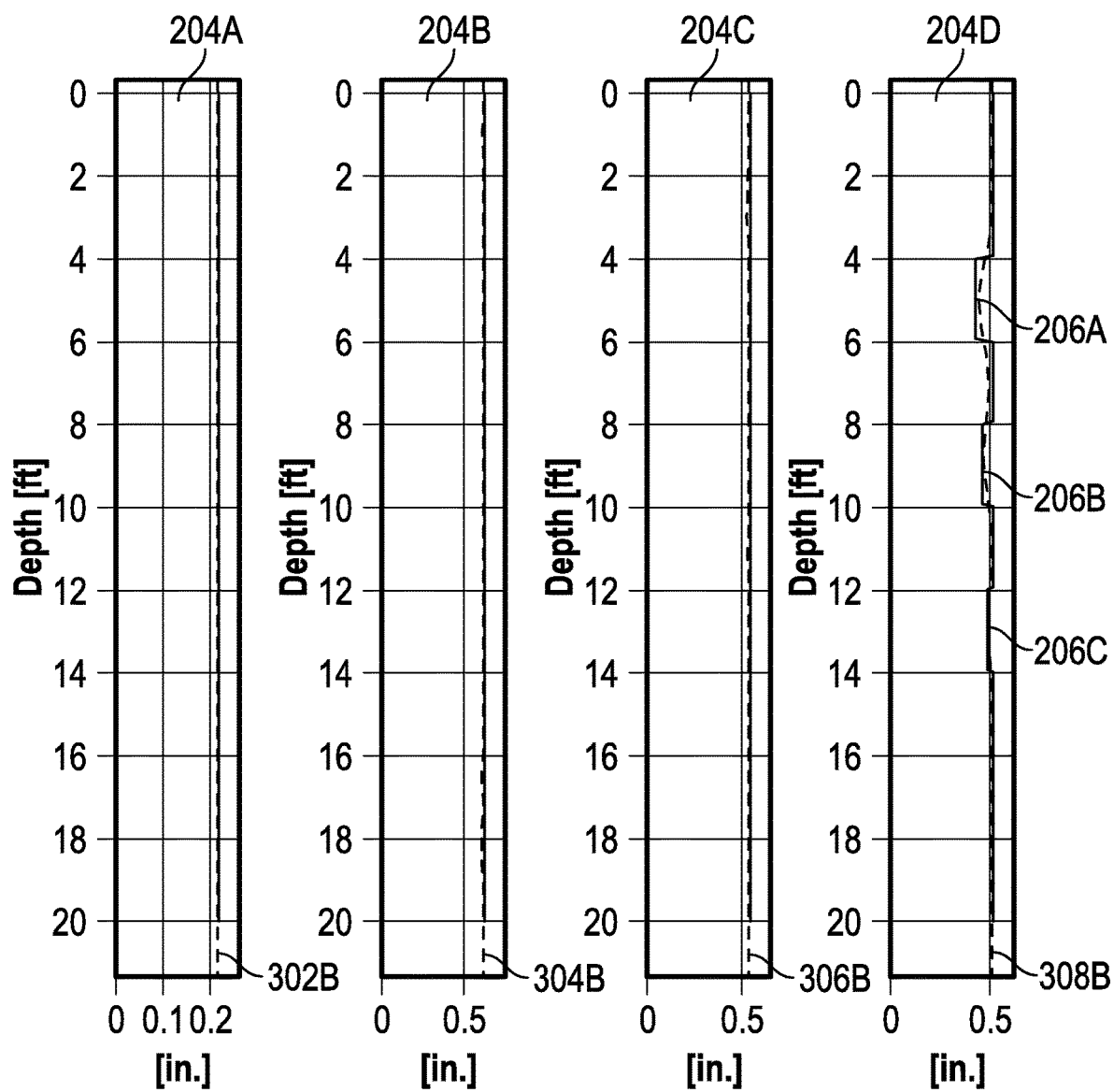
FIG. 12B is a diagram showing actual and predicted defects for the first EM defect detection scenario based on deconvolved raw measurements.

FIG. 12B is a diagram showing actual and predicted defects for the first EM defect detection scenario based on deconvolved raw measurements. As shown in FIG. 12B, the predicted defect lines 302B, 304B, 306B, and 308B (obtained using deconvolved raw measurements) closely resemble the actual defects 206A-206C with regard to both the tubular(s) at issue and the defect locations along the tubular(s). In particular, the predicted defect line 308B indicates that there are thickness variations along tubular 204D, where the location of the thickness variations coincide with the actual defects 206A-206C.

Figures 13A, 13B:
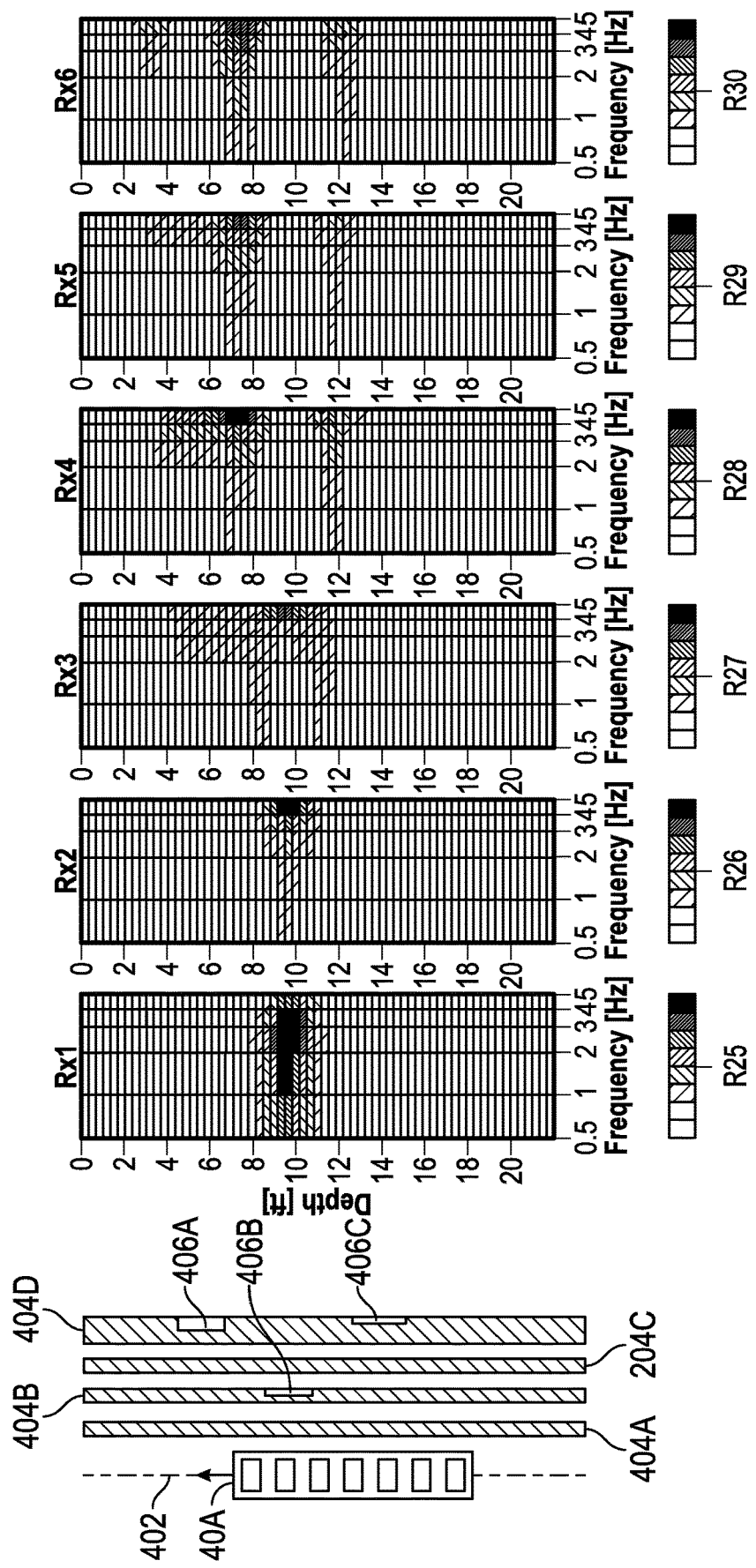
FIG. 13A is a diagram showing an illustrative second EM defect detection scenario.
FIG. 13B is a diagram showing raw magnitude responses for different receivers in the second EM defect detection scenario.

FIG. 13A is a diagram showing an illustrative second EM defect detection scenario. As shown in FIG. 13A, the second EM defect detection scenario corresponds to the EM defect detection tool 40A being deployed in a downhole environment with four tubular strings 404A-404D having different diameters (only a slice of the four tubular strings 404A-404D is shown). Parameters of the tubulars used in the second EM defect detection scenario are summarized in Table 2.

TABLE 1

| Tubular | 404A | 404B | 404C | 404D |
|---|---|---|---|---|
| OD (inches) | 2.875 | 5 | 9.625 | 13.375 |
| Thickness (inches) | 0.217 | 0.625 | .545 | 0.514 |
| Relative μ (estimate) | 62 | 60 | 58 | 82 |
| Length (feet) | 20 | 20 | 20 | 20 |
| Defect(s) | None | 0.05 inches × 2 feet, centered at 9 ft (10%) | None | 0.09 inches × 2 feet, centered at 5 ft (17.5%) 0.03 inches × 2 feet, centered at 13 ft (6%) |

For the second EM defect detection scenario, thickness defects are present in the tubulars strings 404B and 404D. As the EM defect detection tool 40A moves axially along measurement path 402, raw measurements are collected by the EM detect detection tool 40A. For the example given, the EM detect detection tool 40A operates at frequencies ranging from 0.5 Hz to 5 Hz.

FIG. 13B shows illustrative raw magnitude measurements (without deconvolution) for different receivers in the second defect detection scenario. The raw magnitude measurements correspond to the receivers Rx1-Rx6 as a function of axial position along the measurement path 402. In at least some embodiments, the raw magnitude measurements are associated with different frequency ranges (R25-R30), where the frequency ranges may or may not overlap. It should be appreciated that the frequency ranges used for EM defect detection may vary for different EM defect detection tools or scenarios.

Figure 14:
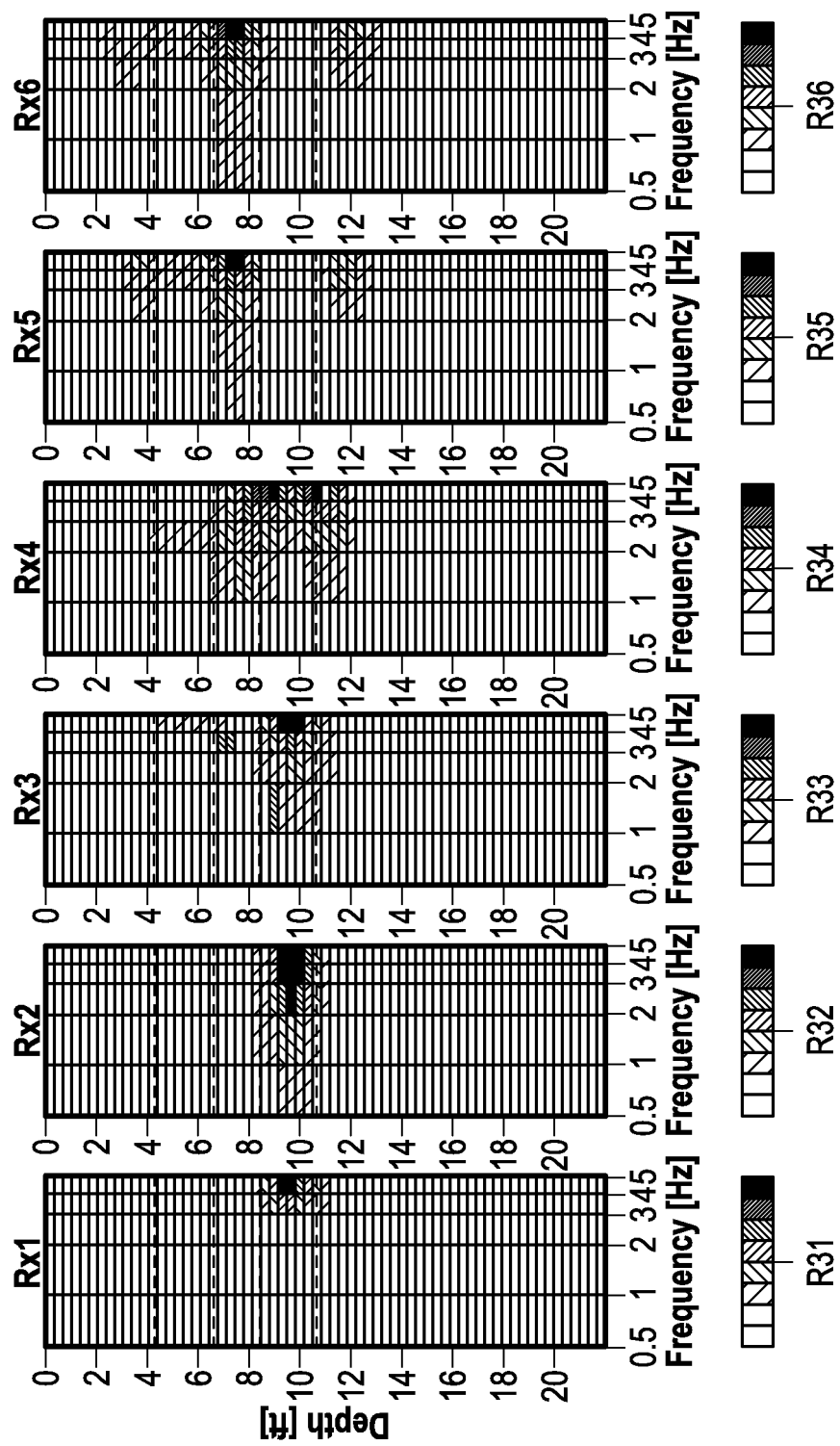
FIG. 14 is a diagram showing raw phase responses for different receivers in the second EM defect detection scenario.

FIG. 14 is a diagram showing raw phase responses (without deconvolution) for different receivers in the second defect detection scenario. The raw phase measurements correspond to receivers Rx1-Rx6 as a function of axial position along the measurement path 402. In at least some embodiments, the raw phase measurements are associated with different frequency ranges (R31-R36), where the frequency ranges may or may not overlap. Again, frequency ranges used for EM defect detection may vary for different EM defect detection tools or scenarios. In FIGS. 13 and 14, the raw measurement responses of the long spacing receivers (e.g., Rx4 through Rx6) are not aligned with the actual defects due to the ghosting effect. To improve defect detection as described herein, deconvolution and other resolution-enhancement techniques (e.g., the resolution-enhancement process 112) are applied.

Figure 15:
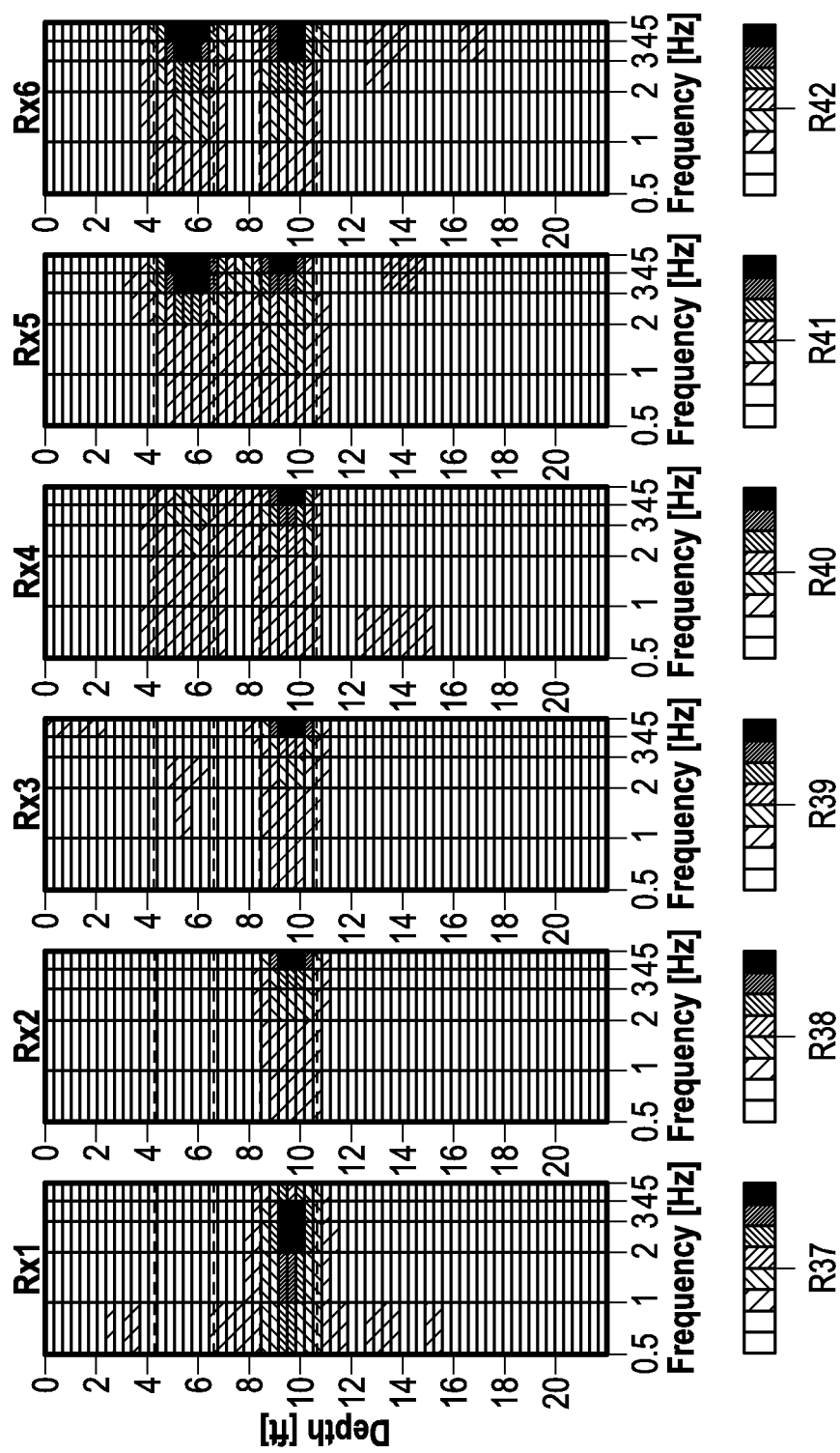
FIG. 15 is a diagram showing deconvolved magnitude responses for different receivers in the second EM defect detection scenario.

FIG. 15 is a diagram showing deconvolved magnitude responses for different receivers in the second defect detection scenario. The deconvolved raw magnitude responses correspond to receivers Rx1-Rx6 as a function of axial position along the measurement path 402. In at least some embodiments, the deconvolved raw magnitude responses are associated with different frequency ranges (R37-R42), where the frequency ranges may or may not overlap. The deconvolved raw magnitude responses may be obtained, for example, using the resolution-enhancement process 112 described previously.

Figure 16:
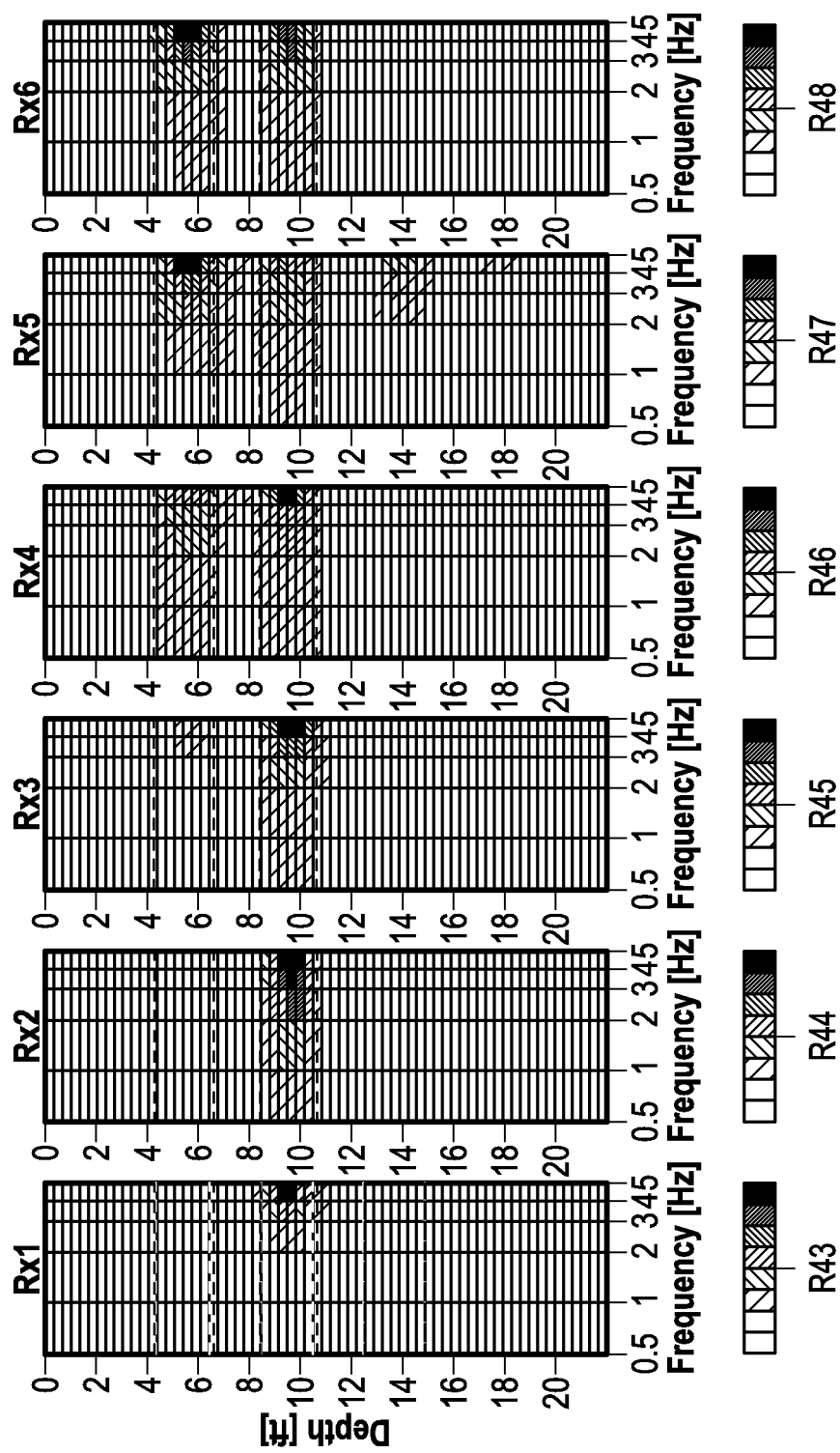
FIG. 16 is a diagram showing deconvolved phase responses for different receivers in the second EM defect detection scenario.

FIG. 16 is a diagram deconvolved raw phase responses for different receivers in the second defect detection scenario. The deconvolved raw phase responses correspond to receivers Rx1-Rx6 as a function of axial position along the measurement path 402. In at least some embodiments, the deconvolved raw phase responses are associated with different frequency ranges (R43-R48), where the frequency ranges may or may not overlap. The deconvolved raw phase responses may be obtained, for example, using the resolution-enhancement process 112 described previously. In FIGS. 15 and 16, the deconvolved raw measurements of the long spacing receivers (e.g., Rx4 through Rx6) are aligned with the actual defects, and can thus improve defect detection as described herein.

Figure 17A:
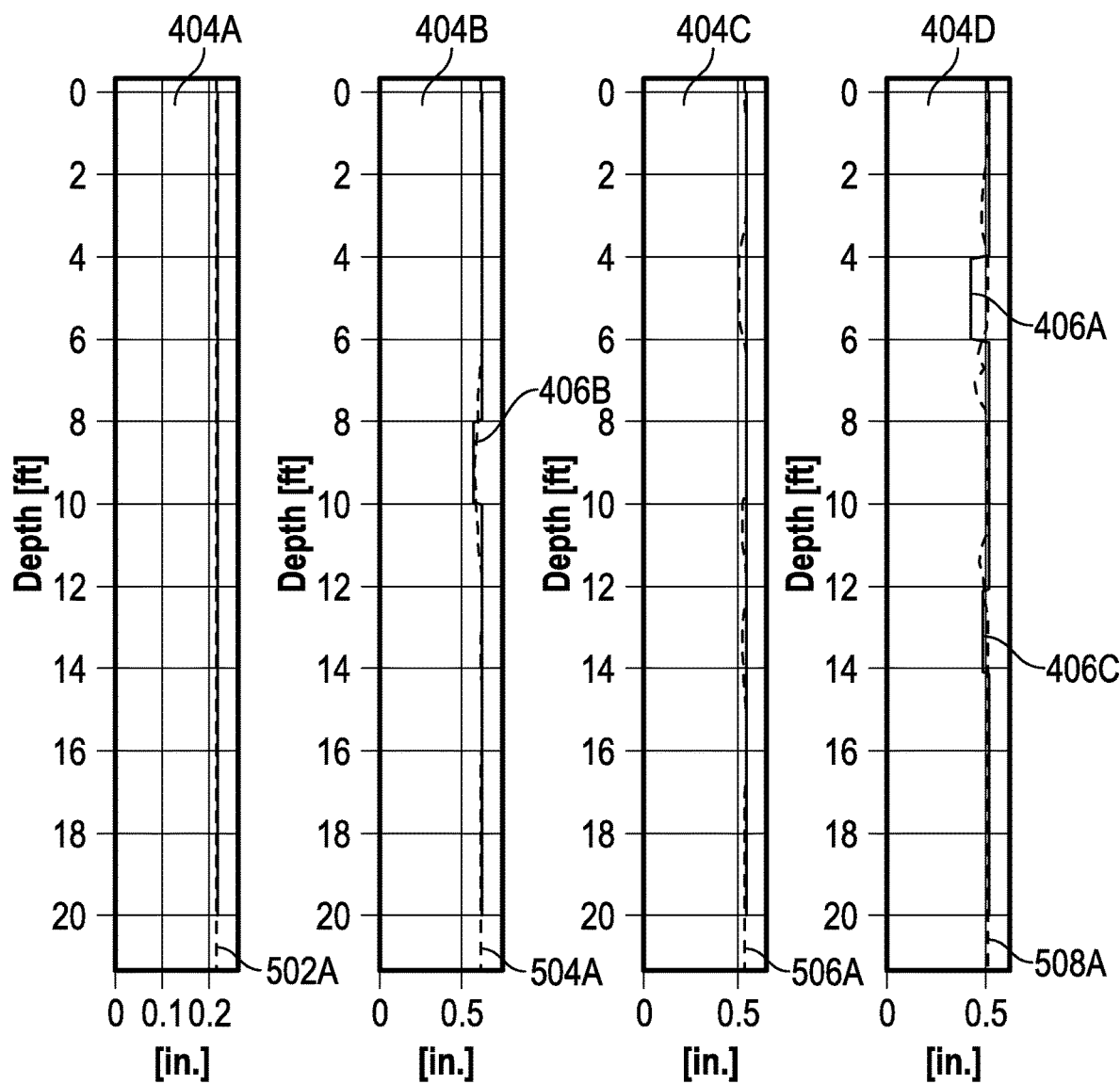
FIG. 17A is a diagram showing actual and predicted defects for the second EM defect detection scenario without deconvolved raw measurements.

FIG. 17A is a diagram showing actual and predicted defects for the second EM defect detection scenario without deconvolved raw measurements. In FIG. 17A, the predicted thickness lines 502A, 504A, 506A, and 508A are based on raw measurements (without deconvolved raw measurements) and result in errors with regard to both the tubular(s) at issue and the defect locations along the tubular(s) relative to the actual defects 406A-406C. In particular, the predicted thickness line 506A incorrectly indicates that there are thickness variations along tubular 404C. Meanwhile, the predicted thickness line 508A correctly indicates that there are thickness variations along tubular 404D, but the location of the thickness variations are incorrect relative to the actual defects 406A and 406C.

Figure 17B:
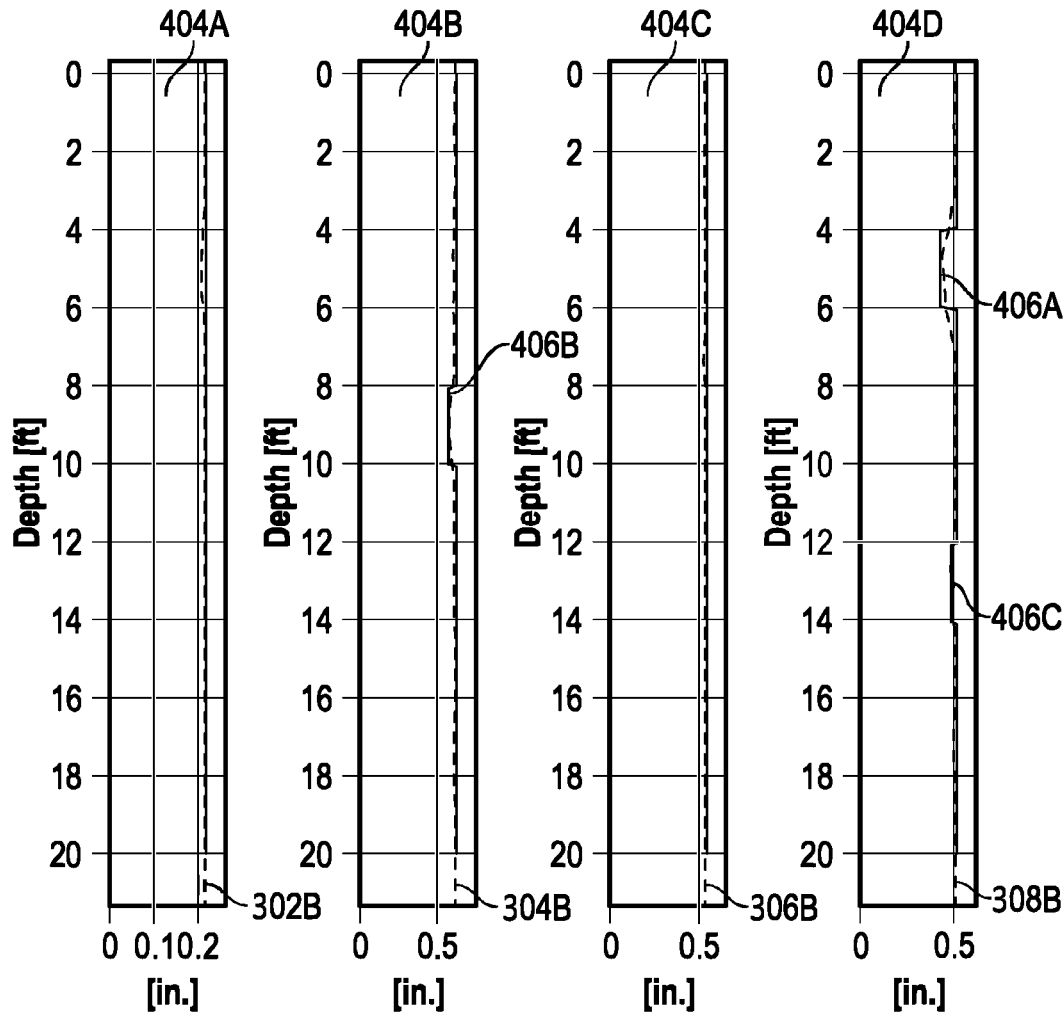
FIG. 17B is a diagram showing actual and predicted defects for the second EM defect detection scenario based on deconvolved raw measurements.

FIG. 17B is a diagram showing actual and predicted defects for the second EM defect detection scenario based on deconvolved raw measurements. As shown in FIG. 17B, the predicted thickness lines 302B, 304B, 306B, and 308B (obtained using deconvolved raw measurements) closely follow the actual defects with regard to both the tubular(s) at issue and the defect locations along the tubular(s) relative to the actual defects 406A-406C. In particular, the predicted thickness line 304B indicates that there are thickness variations along tubular 404B that coincide with the actual defect 406B. The predicted thickness line 308B indicates that there are thickness variations along tubular 404D that coincide with the actual defects 406A and 406C.

Figure 18:
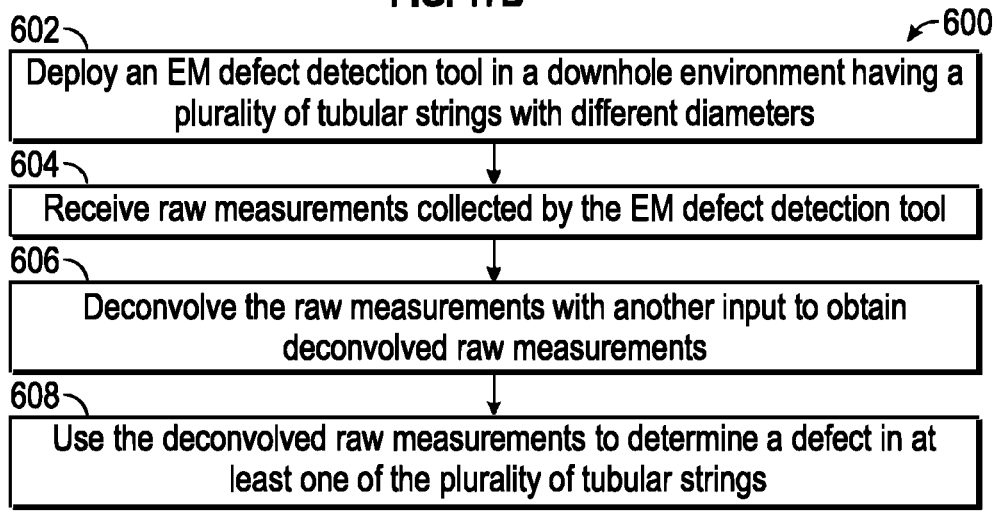
FIG. 18 is a flowchart showing an illustrative method for EM defect detection involving deconvolved raw measurements.

FIG. 18 is a flowchart showing an illustrative method 600 for EM defect detection involving deconvolved raw measurements. At block 602, en EM defect detection tool is deployed in a downhole environment having a plurality of tubular strings with different diameters. At block 604, raw measurements are collected by the EM defect detection tool. At block 606, the raw measurements are deconvolved with another input to obtain deconvolved raw measurements. As described herein, the other input for deconvolution may be an impulse response obtained synthetically (e.g., by modeling a tool response to a representative defect) or from measuring an EM defect detection tool's response to a known defect. At block 608, the deconvolved raw measurements are used to determine a defect in at least one of the plurality of tubular strings. As desired, filtering and/or scaling may be applied to the deconvolved raw measurements the defect determination operations of block 608. In at least some embodiments, defects are determined by performing an inversion to solve for tubular thickness values based at least in part on the deconvolved raw measurements. The inversion used at block 608 may involve R1D processing. In at least some embodiments, the method 600 may perform, by a device, an operation in response to any determined defects. For example, an output device may display a representation of a determined defect. Additionally or alternatively, a flow control device in the well can be adjusted in response to a determined defect. Additionally or alternatively, a well intervention device may be initiated or deployed in the well in response to a determined defect to repair or alter at least one flow path in the well provided by the plurality of tubular strings.

Besides frequency-domain analysis of EM log data as described herein, it should be appreciated that time-domain analysis of EM log data is possible. For time-domain analysis of EM log data, the formulas, workflows, and responses related to EM defect detection (e.g., the resolution-enhancement process 112) would be updated. In either case, deconvolved raw measurements can be relied upon to improve defect detection results. Due to the strong dispersive nature of the problem, there is a relationship between frequency-domain and time-domain measurements associated with the same coils and pipes. In other words, V_time(1/f) is proportional to V_frequency(f), where V_time(t) is the time-domain measurement corresponding to time t, and V_frequency(f) is the frequency domain measurement corresponding to frequency f.

Without limitation to other embodiments, EM defect detection can be based on the assumption that the measurement system is linear. In other words, the response due to any arbitrary defect is assumed to be the convolution of the impulse response (the response due to a small defect) and the response due to a fictional tool with collocated and point-like transmitter and receiver. This assumption holds best for small defects and those on outer pipes.

Embodiments disclosed herein include:

A: A method that comprises deploying an EM defect detection tool in a downhole environment having a plurality of tubular strings with different diameters. The method also comprises receiving raw measurements collected by the EM defect detection tool, and deconvolving the raw measurements with another input to obtain deconvolved raw measurements. The method also comprises using the deconvolved raw measurements to determine a defect in at least one of the plurality of tubular strings. The method also comprises performing, by a device, an operation in response to the determined defect.

B: A system that comprises an EM defect detection tool deployed in downhole environment having a plurality of tubular strings with different diameters. The system also comprises a processing unit that deconvolves raw measurements collected by the EM corrosion detection tool with another input to obtain deconvolved raw measurements. The processing unit determines a defect in at least one of the plurality of tubular strings based at least in part on the deconvolved raw measurements. The system also comprises a device that performs an operation in response to the determined defect.

Each of the embodiments, A and B, may have one or more of the following additional elements in any combination. Element 1: wherein deconvolving the raw measurements with another input comprises determining an impulse response for a representative defect in a tubular, and deconvolving the raw measurements with the determined impulse response to obtain the deconvolved raw measurements. Element 2: wherein determining the impulse response comprises modeling the representative defect in a tubular and a corresponding impulse response using a synthetic model. Element 3: wherein determining the impulse response comprises acquiring measurements corresponding to a known defect in a tubular. Element 4: further comprising filtering the deconvolved raw measurements using a low pass filter, and using the output of said filtering to determine a defect in at least one of the plurality of tubular strings. Element 5: further comprising scaling the deconvolved raw measurements, and using the output of said scaling to determine a defect in at least one of the plurality of tubular strings. Element 6: wherein using the deconvolved raw measurements to determine a defect in at least one of the plurality of tubular strings comprises performing an inversion to solve for tubular thickness values based at least in part on the deconvolved raw measurements. Element 7: further comprising selecting one of the plurality of tubing strings as having a defect based on a comparison of raw measurements collected using different transmitter/receiver spacings or frequencies. Element 8: wherein performing, by a device, an operation in response to the determined defect comprises an output device displaying a representation of the determined defect. Element 9: wherein performing, by a device, an operation in response to the determined defect comprises a flow control device or a well intervention device performing an operation in the well.

Element 10: wherein the processing unit determines or receives an impulse response for a representative defect in a tubular and deconvolves the raw measurements with the impulse response to obtain the deconvolved raw measurements. Element 11: wherein the impulse response is determined from a synthetic model. Element 12: wherein the impulse response is determined from measurements corresponding to a known defect in a tubular. Element 13: wherein the processing unit filters and scales the deconvolved raw measurements to determine a defect in at least one of the plurality of tubular strings. Element 14: wherein the processing unit performs a radial one-dimensional inversion to solve for tubular thickness values based at least in part on the deconvolved raw measurements. Element 15: wherein the processing unit or a user selects one of the plurality of tubing strings as having a defect based on a comparison of raw measurements collected using different transmitter/receiver spacings or frequencies. Element 16: wherein the device that performs an operation in response to the determined defect comprises an output device that displays a representation of the determined defect. Element 17: wherein the device that performs an operation in response to the determined defect comprises a flow control device in the well that adjusts fluid flow based on the determined defect. Element 18: wherein the device that performs an operation in response to the determined defect comprises a well intervention device that is initiated or deployed in response to the determined defect.

Numerous other variations and modifications will become apparent to those skilled in the art once the above disclosure is fully appreciated. For example, the disclosed inversion schemes can be extended to various multi-string scenarios as needed. In at least some embodiments, the order of the processing operations described herein may vary and/or be performed in parallel. It is intended that the following claims be interpreted to embrace all such variations and modifications where applicable.

What is claimed is:

1. A method that comprises:
    deploying an electromagnetic (EM) defect detection tool in a well having a plurality of tubular strings with different diameters;
    receiving raw measurements collected by the EM defect detection tool;
    deconvolving the raw measurements with another input to obtain deconvolved raw measurements;
    scaling the deconvolved raw measurements to bring the deconvolved raw measurements to a same scale as the raw measurements and to produce scaled deconvolved raw measurements;

using the scaled deconvolved raw measurements to determine a defect in at least one of the plurality of tubular strings; and performing, by a device, an operation in response to the determined defect.

2. The method of claim 1, wherein deconvolving the raw measurements with another input comprises:

determining an impulse response for a representative defect in a tubular; and deconvolving the raw measurements with the determined impulse response to obtain the deconvolved raw measurements.

3. The method of claim 2, wherein determining the impulse response comprises modeling the representative defect in a tubular and a corresponding impulse response using a synthetic model.

4. The method of claim 2, wherein determining the impulse response comprises acquiring measurements corresponding to a known defect in a tubular.

5. The method of claim 1, further comprising filtering the deconvolved raw measurements using a low pass filter, and using an output of said filtering to determine a defect in at least one of the plurality of tubular strings.

6. The method of claim 1, wherein using the deconvolved raw measurements to determine a defect in at least one of the plurality of tubular strings comprises performing an inversion to solve for tubular thickness values based at least in part on the deconvolved raw measurements.

7. The method of claim 1, further comprising selecting one of the plurality of tubing strings as having a defect based on a comparison of raw measurements collected using different transmitter/receiver spacings or frequencies.

8. The method of claim 1, wherein performing, by a device, an operation in response to the determined defect comprises an output device displaying a representation of the determined defect.

9. The method of claim 1, wherein performing, by a device, an operation in response to the determined defect comprises a flow control device or a well intervention device performing an operation in the well.

10. A system that comprises:

an electromagnetic (EM) defect detection tool deployed in a well having a plurality of tubular strings with different diameters; and a processing unit configured to:

deconvolve raw measurements collected by the EM defect detection tool with another input to obtain deconvolved raw measurements;

filter and scale the deconvolved raw measurements to bring the deconvolved raw measurements to a same scale as the raw measurements and to produce scaled deconvolved raw measurements; and determine a defect in at least one of the plurality of tubular strings based at least in part on the scaled deconvolved raw measurements; and a device that performs an operation in response to the determined defect.

11. The system of claim 10, wherein the processing unit determines or receives an impulse response for a representative defect in a tubular and deconvolves the raw measurements with the impulse response to obtain the deconvolved raw measurements.

12. The system of claim 11, wherein the impulse response is determined from a synthetic model.

13. The system of claim 11, wherein the impulse response is determined from measurements corresponding to a known defect in a tubular.

14. The system of claim 10, wherein the processing unit performs a radial one-dimensional inversion to solve for tubular thickness values based at least in part on the deconvolved raw measurements.

15. The system of claim 10, wherein the processing unit or a user selects one of the plurality of tubing strings as having a defect based on a comparison of raw measurements collected using different transmitter/receiver spacings or frequencies.

16. The system of claim 10, wherein the device that performs an operation in response to the determined defect comprises an output device that displays a representation of the determined defect.

17. The system of claim 10, wherein the device that performs an operation in response to the determined defect comprises a flow control device in the well that adjusts fluid flow based on the determined defect.

18. The system of claim 10, wherein the device that performs an operation in response to the determined defect comprises a well intervention device that is initiated or deployed in response to the determined defect.

* * * * *